(12) United States Patent
Van Bree et al.

(10) Patent No.: US 7,655,226 B2
(45) Date of Patent: *Feb. 2, 2010

(54) TREATMENT OF POMPE'S DISEASE

(75) Inventors: Johannes B. M. M. Van Bree, Nieuw-Vennep (NL); Edna H. G. Venneker, Saturnushof 15 (NL); David P. Meeker, Concord, MA (US)

(73) Assignee: Genzyme Therapeutic Products Limited Partnership, Cambridge, MA (US)

( * ) Notice: Subject to any disclaimer, the term of this patent is extended or adjusted under 35 U.S.C. 154(b) by 10 days.

This patent is subject to a terminal disclaimer.

(21) Appl. No.: 12/012,003

(22) Filed: Jan. 30, 2008

(65) Prior Publication Data
US 2008/0206223 A1   Aug. 28, 2008

Related U.S. Application Data

(63) Continuation of application No. 10/611,598, filed on Jun. 30, 2003, now Pat. No. 7,351,410, which is a continuation of application No. 09/454,711, filed on Dec. 6, 1999, now abandoned.

(60) Provisional application No. 61/111,291, filed on Dec. 7, 1998, provisional application No. 60/001,796, filed on Aug. 2, 1995.

(51) Int. Cl.
A61K 38/46 (2006.01)
A61K 38/43 (2006.01)

(52) U.S. Cl. ............... 424/94.61; 424/94.1; 424/94.6; 435/183; 435/200; 435/201

(58) Field of Classification Search ........... 435/183, 435/200, 201; 424/94.1, 94.6, 94.61
See application file for complete search history.

(56) References Cited

U.S. PATENT DOCUMENTS

| | | | |
|---|---|---|---|
| 5,356,804 | A | 10/1994 | Desnick et al. |
| 5,565,362 | A | 10/1996 | Rosen |
| 6,118,045 | A | 9/2000 | Reuser et al. |

FOREIGN PATENT DOCUMENTS

| | | |
|---|---|---|
| WO | WO 93/25567 A | 12/1993 |
| WO | WO 97/05571 | 2/1997 |

OTHER PUBLICATIONS

Nema et al., "Excipients and Their Use in Injectable Products", PDA J of Pharm Sci & Tech,vol. 51, No. 4, Jul.-Aug. 1997, p. 167-171.*
Barnes, A.K. and C.H. Wynn, "Homology of Lysosomal Enzymes and Related Proteins: Prediction of Posttranslational Modification Site Including Phosphorylation of Mannose and Potential Epitopic and Substrate Binding Sites in the α- and β-Subunits of Hexosamindases, α-Glucosidase, and Rabbit and Human Isomaltase," *Proteins: Structure, Function, and Genetics*, 4:182-189 (1988).
Belen'kii, D.M., et al., "Purification and Properties of Acid α-Glucosidase (γ-Amylase) from Human Liver," Translated from: *Biokhimiya*, 40:927-933 (1975).
Bijvoet, A.G., et al., "Expression of cDNA-Encoded Human Acid α-Glucosidase in Milk of Transgenic Mice," *Biochimica and Biophysica Acta*, 1308:93-96 (1996).
Bresciani, R., et al., "Lysosomal Acid Phosphatase is not Involved in the Dephosphorylation of Mannose 6-Phosphate Containing Lysosomal Proteins," *Eur. J. of Cell Biol.*, 58:57-61 (1992).
de Barsy, T., et al. "Enzyme Replacement in Pompe Disease; An Attempt with Purified Human Acid Alpha Glucosidase," *Birth Defects Original Article Series*, 9:1840190 (1973).
Hoefsloot, L.H., et al., "Expression and Routing of Human Lysosomal α-Glucosidase in Transiently Transfected Mammalian Cells," *Biochemica Journal*, 272:485-492 (1990).
Houdebine, L.M., "Production of Pharmaceutical Proteins from Transgenic Animals," *J. of Biotech.*, 34:269-287 (1994).
Kichuchi, T., et al. "Clinical and Metabolic Correction of Pompe Disease by Enzyme Therapy in Acid Maltase-Deficient Quail," *J. Clin. Invest.*, 101:827-833 (1998).
Minamiura, N., et al., "Identity of α-Glucosidase of Human Kidney with Urine F-1 α-Glucosidase," *J. Biochemistry*, 91:809-816 (1982).
Obara, Y., et al., "Mutual Relationship Between Milk Components and Lysosome Enzymatic Activity in Abnormal Milk," *Japanese Journal of Veterinary Science*, 45:203-208 (1983).
Oberkotter, L.V., et al. "N-acetyl-β-Hexosaminadase Activity in Human Breast Milk," *International Journal of Biochemistry*, 14:151-154 (1982).
Platenburg, G., et al., "Expression of human Lactoferrin in Milk of Transgenic Mice," *Transgenic Research*, 3:99-108 (1994).
Rochefort, H., et al., "The Estrogen-Regulated 52K-Cathepsin-D in Breast Cancer: From Biology to Clinical Applications," *Nuclear Medicine and Biology*, 14:377-384 (1987).
Van der Ploeg, A.T., et al., "Intravenous Administration of Phosphorylated Acid α-Glucosidase Leads to Update of Enzyme in Heart and Skeletal Muscle of Mice," *The Journal of Clinical Investigation*, 87:513-518 (1991).
Van Hove, J.L.K., et al., "Purification of Recombinant Human Precursor Acid Alpha Glucosidase, Biochemistry and Molecular Biology International," 43:613-623 (1997).
Bijvoet, A.G.A., et al., "Recombinant Human Acid ÿ-Glucosidase: High Level Production in Mouse Milk, Biochemical Characteristics, Correction of Enzyme Deficiency in GSDII KO Mice," Hum. Mol. Genet. 7(11): 1815024 (1998).
Fuller, M., et al., "Isolation and Characterisation of a Recombinant, Precursor Form of Lysosomal Acid ÿ-Glucosidase," Eur. J. Biochem., 234: 903-909 (1995).
Hoefsloot, L.H., et al., "Primary Structure and Processing of Lysosomal ÿ-Glucosidase; Homology with the Intestinal Sucrase-Isomaltase Complex," EMBO, 7(6); 1697-1704 (1988).

(Continued)

*Primary Examiner*—Ruth A Davis
(74) *Attorney, Agent, or Firm*—Hamilton, Brook, Smith & Reynolds, P.C.

(57) ABSTRACT

The invention provides methods of treating Pompe's disease using human acid alpha glucosidase. A preferred treatment regime comprises administering greater than 10 mg/kg body weight per week to a patient.

6 Claims, 7 Drawing Sheets

OTHER PUBLICATIONS

Martiniuk, F., et al., "Recombinant Human Acid ÿ-Glucosidase Generated in Bacteria: Antigenic, but Enzymatically Inactive," DNA and Cell Biol. 11(9): 701-706 (1992).

Yang, H.W., et al., "Recombinant Human Acid ÿ-Glucosidase Corrects Acid ÿ-Glucosidase-Deficient Human Fibroblasts, Quail Fibroblasts, and Quail Myoblasts," Pediatr. Res., 43(3) 374-80 (1998).

Van Hove, J.L.K., et al., "High-Level Production of Recombinant Human Lysosomal Acid ÿ-Glucosidase in Chinese Hamster Ovary Cells Which Targets to Heart Muscle and Corrects Glycogen Accumulation in Fibroblasts from Patient with Pompe Disease," Proc. Natl. Acad. Sci. 93: 65-70 (1996).

Raben, N., et al., "Targeted Disruption of the Acid ÿ-Glucosidase Gene in Mice Causes an Illness with Critical Features of Both Infantile and Adult Human Glycogen Storage Disease Type II," J. Biol. Chem., 272(30): 19086-19092 (1998).

Byrne, B.J., et al., "Reconstitution of Acid Alpha-Glucosidase Activity in a Mouse Model of Cardioskeletal Myopathy, Pompe's Disease," *Circulation*, vol. 98, No. 17 Suppl., Oct. 27, 1998, p. 1737, XP001041662 & 71st Scientific Sessions of the American Heart Association; Dallas, Texas, USA; Nov. 8-11, 1998 ISSN: 0009-7322.

Mutsaers, J.H.G.M., et al, "Determination of the Structure of the Carbohydrate Claims of Acid α-Glucosidase from Human Placenta," *Biochemica et Biophysica Acta* 911:244-251 (1987).

Yang, H.W., et al., "Recombinant Human α-Glucosidase Corrects Acid α-Glucosidase-Deficient Human Fibroblasts, Quail Fibroblasts, and Quail Myoblasts," *American Journal of Human Genetics*, vol. 59: No. 4 Suppl., (1996), p. A209, XP000934192 & 4th Annual Meeting of the American Society of Human Genetics; San Francisco, CA, USA; Oct. 29-Nov. 2, 1996 ISSN: 0002-9297.

Williams, et al. "Enzyme Replacement in Pompe Disease With an α-Glucosidase-Low Density Lipoprotein Complex," *Birth Defects: Original Article Series* XVI:415-423 (1980).

* cited by examiner

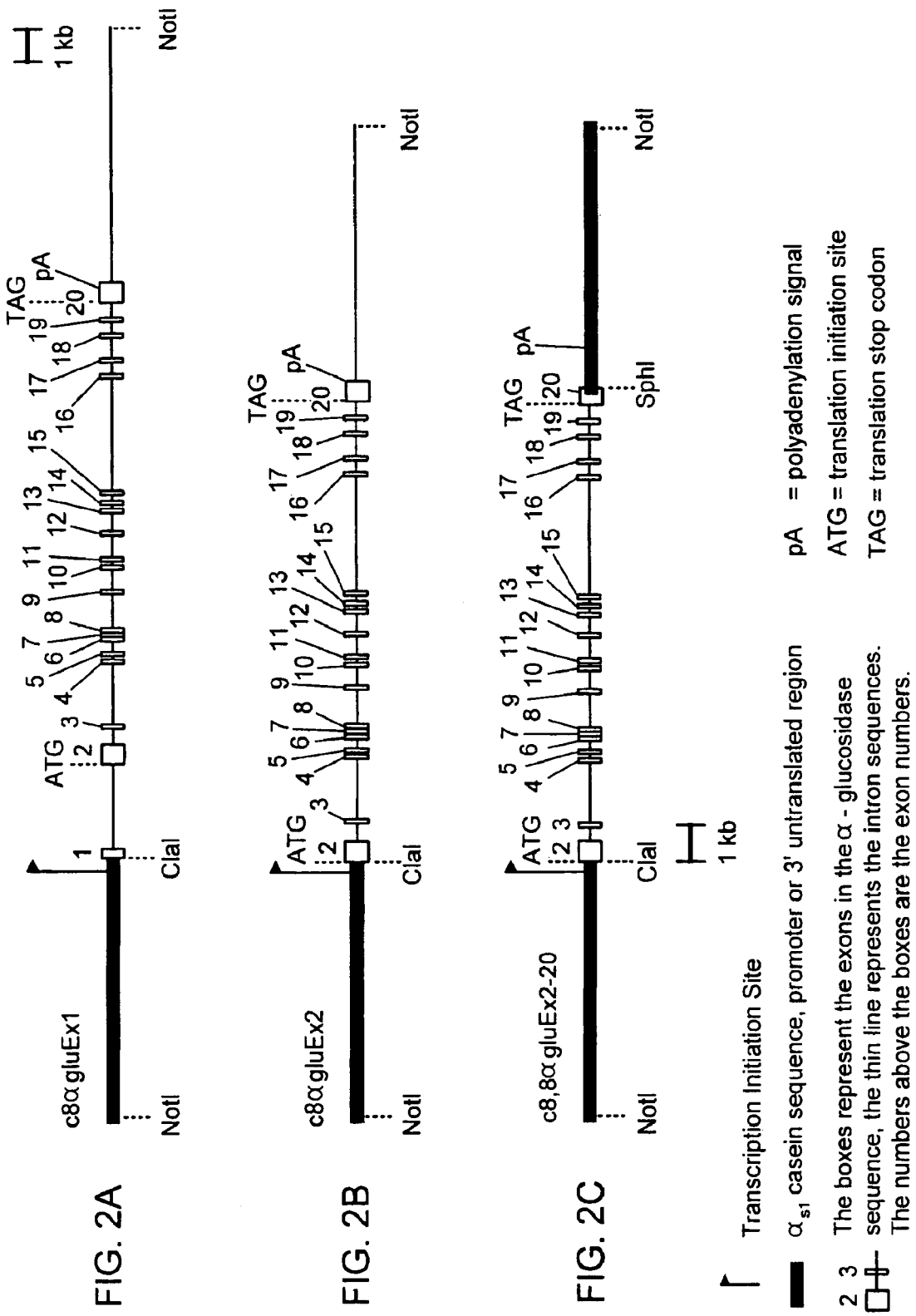

TREATMENT OF POMPE'S DISEASE

RELATED APPLICATIONS

This application is a continuation of U.S. application Ser. No. 10/611,598, filed Jun. 30, 2003 now U.S. Pat. No. 7,351,410 which is a continuation of U.S. application Ser. No. 09/454,711, filed Dec. 6, 1999, now abandoned which claims the benefit of U.S. Provisional Application No. 60/111,291 filed Dec. 7, 1998, which is related to U.S. application Ser. No. 08/700,760 filed Jul. 29, 1996, now U.S. Pat. No. 6,118,045, which claims the benefit of U.S. Provisional Application No. 60/001,796, filed Aug. 2, 1995. The entire teachings of the above applications are incorporated herein by reference.

TECHNICAL FIELD

The present invention resides in the fields of recombinant genetics, and medicine, and is directed to enzyme-replacement therapy of patients with Pompe's disease.

BACKGROUND OF THE INVENTION

Like other secretory proteins, lysosomal proteins are synthesized in the endoplasmic reticulum and transported to the Golgi apparatus. However, unlike most other secretory proteins, the lysosomal proteins are not destined for secretion into extracellular fluids but into an intracellular organelle. Within the Golgi, lysosomal proteins undergo special processing to equip them to reach their intracellular destination. Almost all lysosomal proteins undergo a variety of posttranslational modifications, including glycosylation and phosphorylation via the 6' position of a terminal mannose group. The phosphorylated mannose residues are recognized by specific receptors on the inner surface of the Trans Golgi Network. The lysosomal proteins bind via these receptors, and are thereby separated from other secretory proteins. Subsequently, small transport vesicles containing the receptor-bound proteins are pinched off from the Trans Golgi Network and are targeted to their intracellular destination. See generally Kornfeld, Biochem. Soc. Trans. 18, 367-374 (1990).

There are over thirty lysosomal diseases, each resulting from a deficiency of a particular lysosomal protein, usually as a result of genetic mutation. See, e.g., Cotran et al., Robbins Pathologic Basis of Disease (4th ed. 1989) (incorporated by reference in its entirety for all purposes). The deficiency in the lysosomal protein usually results in harmful accumulation of a metabolite. For example, in Hurler's, Hunter's, Morquio's, and Sanfilippo's syndromes, there is an accumulation of mucopolysaccharides; in Tay-Sachs, Gaucher, Krabbe, Niemann-Pick, and Fabry syndromes, there is an accumulation of sphingolipids; and in fucosidosis and mannosidosis, there is an accumulation of fucose-containing sphingolipids and glycoprotein fragments, and of mannose-containing oligosaccharides, respectively.

Glycogen storage disease type II (GSD II; Pompe disease; acid maltase deficiency) is caused by deficiency of the lysosomal enzyme acid α-glucosidase (acid maltase). Two clinical forms are distinguished: early onset infantile and late onset, juvenile and adult. Infantile GSD II has its onset shortly after birth and presents with progressive muscular weakness and cardiac failure. This clinical variant is usually fatal within the first two years of life. Symptoms in the late onset in adult and juvenile patients occur later in life, and only skeletal muscles are involved. The patients eventually die due to respiratory insufficiency. Patients may exceptionally survive for more than six decades. There is a good correlation between the severity of the disease and the residual acid α-glucosidase activity, the activity being 10-20% of normal in late onset and less than 2% in early onset forms of the disease (see Hirschhorn, The Metabolic and Molecular Bases of Inherited Disease (Scriver et al., eds., 7th ed., McGraw-Hill, 1995), pp. 2443-2464).

Since the discovery of lysosomal enzyme deficiencies as the primary cause of lysosomal storage diseases (see, e.g., Hers, Biochem. J. 86, 11-16 (1963)), attempts have been made to treat patients having lysosomal storage diseases by (intravenous) administration of the missing enzyme, i.e., enzyme therapy. These experiments with enzyme replacement therapy for Pompe's disease were not successful. Either non-human α-glucosidase from Aspergillus niger, giving immunological reactions, or a form of the enzyme that is not efficiently taken up by cells (the low uptake form, mature enzyme from human placenta; see below) was used. Moreover, both the duration of treatment, and/or the amount of enzyme administered were insufficient (3-5). Production of lysosomal enzymes from natural sources such as human urine and bovine testis is in theory possible, but gives low yields, and the enzyme purified is not necessarily in a form that can be taken up by tissues of a recipient patient.

Notwithstanding the above uncertainties and difficulties, the invention provides methods of treating patients for Pompe's disease using human acid alpha glucosidase.

SUMMARY OF THE INVENTION

In one aspect, the invention provides methods of treating a patient with Pompe's disease. Such methods entail administering to the patient a therapeutically effective amount of human acid alpha glucosidase. The dosage is preferably at least 10 mg/kg body weight per week. In some methods, the dosage is at least 60 mg/kg body weight per week or at least 120 mg/kg body weight per week. In some methods, such dosages are administered on a single occasion per week and in other methods on three occasions per week. In some methods, the treatment is continued for ate least 24 weeks. Administration is preferably intravenous. The human acid alpha glucosidase is preferably obtained in the milk of a nonhuman transgenic mammal, and is preferably predominantly in a 110 kD form.

The methods can be used for treating patients with infantile, juvenile or adult Pompe's disease. In some methods of treating infantile Pompe's disease efficacy is indicated by a patient surviving to be at least one year old.

In some methods, levels of human acid alpha glucosidase are monitored in the patient. Optionally, a second dosage of human acid alpha glucosidase can be administered if the level of alpha-glucosidase falls below a threshold value in the patient.

In some methods, the human alpha glucosidase is administered intravenously and the rate of administration increases during the period of administration. In some methods, the rate of administration increases by at least a factor of ten during the period of administration. In some methods, the rate of administration increases by at least a factor of ten within a period of five hours. In some methods, the patient is administered a series of at least four dosages, each dosage at a higher strength than the previous dosage. In some methods, the dosages are a first dosage of 0.03-3 mg/kg/hr, a second dosage of 0.3-12 mg/kg/hr, a third dosage of 1-30 mg/kg/hr and a fourth dosage of 2-60 mg/kg/hr. In some methods, the dosages are a first dosage of 0.1-1 mg/kg/hr, a second dosage of 14 mg/kg/hr, a third dosage of 3-10 mg/kg/hr and a fourth dosage of 6-20 mg/kg/hr. In some methods, the dosages are a first dosage of 0.254 mg/kg/hr, a second dosage of 0.9-1.4 mg/kg/hr, a third dosage of 3.6-5.7 mg/kg/hr and a fourth dosage of 7.211.3 mg/kg/hr. In some methods, the dosages are a first dosage of 0.3 mg/kg/hr, a second dosage of 1 mg/kg/hr, a third dosage of 4 mg/kg/hr and a fourth dosage of 12 mg/kg/hr. In some methods, the first, second, third and fourth dosages are each administered for periods of 15 min to 8 hours.

In some methods, the first, second, third and fourth dosages are administered for periods of 1 hr, 1 hr, 0.5 hr and 3 hr respectively.

In another aspect, the invention provides a pharmaceutical composition comprising human acid alpha glucosidase, human serum albumin, and a sugar in a physiologically acceptable buffer in sterile form. Some such compositions comprise human acid alpha glucosidase, human serum albumin, and glucose in sodium phosphate buffer. Some compositions comprise alpha glucosidase, mannitol and sucrose in an aqueous solution. In some compositions, the sugar comprises mannitol and sucrose and the concentration of mannitol is 1-3% w/w of the aqueous solution and the concentration of sucrose is 0.1 to 1% w/w of the aqueous solution. In some compositions, the concentration of mannitol is 2% w/w and the concentration of sucrose is 0.5% w/w.

The invention further provides a lyophilized composition produced by lyophilizing a pharmaceutical composition comprising human acid glucosidase, mannitol and sucrose in aqueous solution. Such a composition can be prepared by lyophilizing a first composition comprising human acid alpha-glucosidase, mannitol, sucrose and an aqueous solution to produce a second composition; and reconstituting the lyophilized composition in saline to produce a third composition. In some such compositions, the human acid alpha-glucosidase is at 5 mg/ml in both the first and third composition, the mannitol is at 2 mg/ml in the first composition, the sucrose is at 0.5 mg/ml in the first composition, and the saline used in the reconstituting step is 0.9% w/w.

BRIEF DESCRIPTION OF THE DRAWINGS

FIG. 2 (panels A, B, C): Three transgenes containing acid α-glucosidase genomic DNA. Dark shaded areas are αs1 casein sequences, open boxes represent acids α-glucosidase exons, and the thin line between the open boxes represents α-glucosidase introns. Other symbols are the same as in FIG. 1

DEFINITIONS

Figure 1:
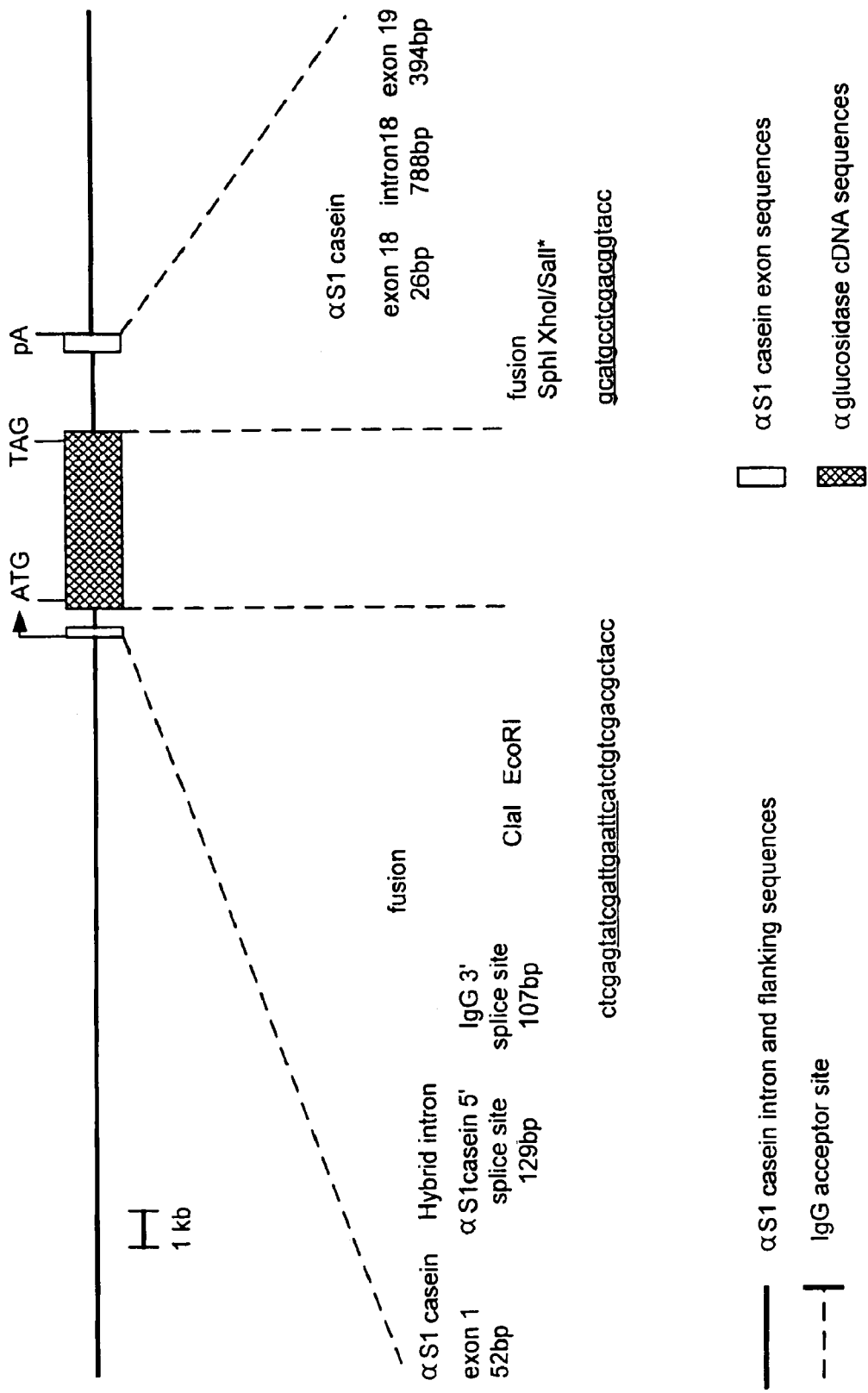
FIG. 1: A transgene containing acid α-glucosidase cDNA. The αs1-casein exons are represented by open boxes; α-glucosidase cDNA is represented by a shaded box. The αs1-casein intron and flanking sequences (SEQ ID NOS:2 and 3) are represented by a thick line. A thin line represents the IgG acceptor site. The transcription initiation site is marked (1→), the translation initiation site (ATG), the stop codon (TAG) and the polyadenylation site (pA).

The term "substantial identity" or "substantial homology" means that two peptide sequences, when optimally aligned, such as by the programs GAP or BESTFIT using default gap weights, share at least 65 percent sequence identity, preferably at least 80 or 90 percent sequence identity, more preferably at least 95 percent sequence identity or more (e.g., 99 percent sequence identity). Preferably, residue positions which are not identical differ by conservative amino acid substitutions.

The term "substantially pure" or "isolated" means an object species has been identified and separated and/or recovered from a component of its natural environment. Usually, the object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a substantially pure composition will comprise more than about 80 to 90 percent by weight of all macromolecular species present in the composition. Most preferably, the object species is purified to essential homogeneity (contaminant species cannot be detected in the composition by conventional detection methods) wherein the composition consists essentially of derivatives of a single macromolecular species.

A DNA segment is operably linked when placed into a functional relationship with another DNA segment. For example, DNA for a signal sequence is operably linked to DNA encoding a polypeptide if it is expressed as a preprotein that participates in the secretion of the polypeptide; a promoter or enhancer is operably linked to a coding sequence if it stimulates the transcription of the sequence. Generally, DNA sequences that are operably linked are contiguous, and in the case of a signal sequence both contiguous and in reading phase. However, enhancers need not be contiguous with the coding sequences whose transcription they control. Linking is accomplished by ligation at convenient restriction sites or at adapters or linkers inserted in lieu thereof.

An exogenous DNA segment is one foreign to the cell, or homologous to a DNA segment of the cell but in an unnatural position in the host cell genome. Exogenous DNA segments are expressed to yield exogenous polypeptides.

In a transgenic mammal, all, or substantially all, of the germline and somatic cells contain a transgene introduced into the mammal or an ancestor of the mammal at an early embryonic stage.

DETAILED DESCRIPTION

The invention provides transgenic nonhuman mammals secreting a lysosomal protein into their milk. Secretion is achieved by incorporation of a transgene encoding a lysosomal protein and regulatory sequences capable of targeting expression of the gene to the mammary gland. The transgene is expressed, and the expression product posttranslationally modified within the mammary gland, and then secreted in milk. The posttranslational modification can include steps of glycosylation and phosphorylation to produce a mannose-6 phosphate containing lysosomal protein.

A. Lysosomal Genes

The invention provides transgenic nonhuman mammals expressing DNA segments containing any of the more than 30 known genes encoding lysosomal enzymes and other types of lysosomal proteins, including α-glucosidase, α-L-iduronidase, iduronate-sulfate sulfatase, hexosaminidase A and B, ganglioside activator protein, arylsulfatase A and B, iduronate sulfatase, heparan N-sulfatase, galacto-ceramidase, α-galactosylceramidase A, sphingomyelinase, α-fucosidase, α-mannosidase, aspartylglycosamine amide hydrolase, acid lipase, N-acetyl-a-D-glucosamine-6-sulphate sulfatase, α- and β-galactosidase, β-glucuronidase, β-mannosidase, ceramidase, galacto-cerebrosidase, α-N-acetylgalactosaminidase, and protective protein and others. Transgenic mammals expressing allelic, cognate and induced variants of any of the known lysosomal protein gene sequences are also included. Such variants usually show substantial sequence identity at the amino acid level with known lysosomal protein genes. Such variants usually hybridize to a known gene under stringent conditions or crossreact with antibodies to a polypeptide encoded by one of the known genes.

DNA clones containing the genomic or cDNA sequences of many of the known genes encoding lysosomal proteins are available. (Scott et al., Am. J. Hum. Genet. 47, 802-807 (1990); Wilson et al., PNAS 87, 8531-8535 (1990); Stein et al., J. Biol. Chem. 264, 1252-1259 (1989); Ginns et al., Biochem. Biophys. Res. Comm. 123, 574-580 (1984); Hoefsloot et al., EMBO J. 7, 1697-1704 (1988); Hoefsloot et al., Biochem. J. 272, 473-479 (1990); Meyerowitz and Proia, PNAS 81, 5394-5398 (1984); Scriver et al., supra, part 12, pages 2427-2882 and references cited therein)) Other examples of genomic and cDNA sequences are available from GenBank. To the extent that additional cloned sequences of lysosomal genes are required, they may be obtained from genomic or cDNA libraries (preferably human) using known lysosomal protein DNA sequences or antibodies to known lysosomal proteins as probes.

B. Conformation of Lysosomal Proteins

Recombinant lysosomal proteins are preferably processed to have the same or similar structure as naturally occurring lysosomal proteins. Lysosomal proteins are glycoproteins that are synthesized on ribosomes bound to the endoplasmic reticulum (RER). They enter this organelle co-translationally guided by an N-terminal signal peptide (Ng et al., Current Opinion in Cell Biology 6, 510-516 (1994)). The N-linked glycosylation process starts in the RER with the en bloc transfer of the high-mannose oligosaccharide precursor Glc3Man9GlcNAc2 from a dolichol carrier. Carbohydrate chain modification starts in the RER and continue in the Golgi apparatus with the removal of the three outermost glucose residues by glycosidases I and II. Phosphorylation is a two-step procedure in which first N-acetyl-gluco-samine-1-phosphate is coupled to select mannose groups by a lysosomal protein specific transferase, and second, the N-acetyl-glucosamine is cleaved by a diesterase (Goldberg et al., Lysosomes: Their Role in Protein Breakdown (Academic Press Inc., London, 1987), pp. 163-191). Cleavage exposes mannose 6-phosphate as a recognition marker and ligand for the mannose 6-phosphate receptor mediating transport of most lysosomal proteins to the lysosomes (Kornfeld, Biochem. Soc. Trans. 18, 367-374 (1992)).

In addition to carbohydrate chain modification, most lysosomal proteins undergo proteolytic processing, in which the first event is removal of the signal peptide. The signal peptide of most lysosomal proteins is cleaved after translocation by signal peptidase after which the proteins become soluble. There is suggestive evidence that the signal peptide of acid α-glucosidase is cleaved after the enzyme has left the RER, but before it has entered the lysosome or the secretory pathway (Wisselaar et al., J. Biol. Chem. 268, 2223-2231 (1993)). The proteolytic processing of acid at-glucosidase is complex and involves a series of steps in addition to cleavage of the signal peptide taking place at various subcellular locations. Polypeptides are cleaved off at both the N and C terminal ends, whereby the specific catalytic activity is increased. The main species recognized are a {fraction ($110/100$)} kD precursor, a 95 kD intermediate and 76 kD and 70 kD mature forms. (Hasilik et al., J. Biol. Chem. 255, 4937-4945 (1980); Oude Elferink et al., Eur. J. Biochem. 139, 489-495 (1984); Reuser et al., J. Biol. Chem. 260, 8336-8341 (1985); Hoefsloot et al., EMBO J. 7, 1697-1704 (1988)). The post translational processing of natural human acid α-glucosidase and of recombinant forms of human acid α-glucosidase as expressed in cultured mammalian cells like COS cells, BHK cells and CHO cells is similar (Hoefsloot et al., (1990) supra; Wisselaar et al., (1993) supra.

Authentic processing to generate lysosomal proteins phosphorylated at the 6' position of the mannose group can be tested by measuring uptake of a substrate by cells bearing a receptor for mannose 6-phosphate. Correctly modified substrates are taken up faster than unmodified substrates, and in a manner whereby uptake of the modified substrate can be competitively inhibited by addition of mannose 6-phosphate.

C. Transgene Design

Transgenes are designed to target expression of a recombinant lysosomal protein to the mammary gland of a transgenic nonhuman mammal harboring the transgene. The basic approach entails operably linking an exogenous DNA segment encoding the protein with a signal sequence, a promoter and an enhancer. The DNA segment can be genomic, minigene (genomic with one or more introns omitted), cDNA, a YAC fragment, a chimera of two different lysosomal protein genes, or a hybrid of any of these. Inclusion of genomic sequences generally leads to higher levels of expression. Very high levels of expression might overload the capacity of the mammary gland to perform posttranslation modifications, and secretion of lysosomal proteins. However, the data presented below indicate that substantial posttranslational modification occurs including the formation of mannose 6-phosphate groups, notwithstanding a high expression level in the mg/ml range. Substantial modification means that at least about 10, 25, 50, 75 or 90% of secreted molecules bear at least one mannose 6-phosphate group. Thus, genomic constructs or hybrid cDNA-genomic constructs are generally preferred.

In genomic constructs, it is not necessary to retain all intronic sequences. For example, some intronic sequences can be removed to obtain a smaller transgene facilitating DNA manipulations and subsequent microinjection. See Archibald et al., WO 90/05188 (incorporated by reference in its entirety for all purposes). Removal of some introns is also useful in some instances to reduce expression levels and thereby ensure that posttranslational modification is substantially complete. In other instances excluding an intron such as intron one from the genomic sequence of acid α-glucosidase leads to a higher expression of the mature enzyme. It is also possible to delete some or all of noncoding exons. In some transgenes, selected nucleotides in lysosomal protein encoding sequences are mutated to remove proteolytic cleavage sites.

Because the intended use of lysosomal proteins produced by transgenic mammals is usually administration to humans, the species from which the DNA segment encoding a lysosomal protein sequence is obtained is preferably human. Analogously if the intended use were in veterinary therapy (e.g., on a horse, dog or cat), it is preferable that the DNA segment be from the same species.

The promoter and enhancer are from a gene that is exclusively or at least preferentially expressed in the mammary gland (i.e., a mammary-gland specific gene). Preferred genes as a source of promoter and enhancer include β-casein, κ-casein, αS1-casein, αS2-casein, β-lactoglobulin, whey acid protein, and α-lactalbumin. The promoter and enhancer are usually but not always obtained from the same mammary-gland specific gene. This gene is sometimes but not necessarily from the same species of mammal as the mammal into which the transgene is to be expressed. Expression regulation sequences from other species such as those from human genes can also be used. The signal sequence must be capable of directing the secretion of the lysosomal protein from the mammary gland. Suitable signal sequences can be derived from mammalian genes encoding a secreted protein. Surprisingly, the natural signal sequences of lysosomal proteins are suitable, notwithstanding that these proteins are normally not secreted but targeted to an intracellular organelle. In addition to such signal sequences, preferred sources of signal sequences are the signal sequence from the same gene as the promoter and enhancer are obtained. Optionally, additional regulatory sequences are included in the transgene to optimize expression levels. Such sequences include 5' flanking regions, 5' transcribed but untranslated regions, intronic sequences, 3' transcribed but untranslated regions, polyadenylation sites, and 3' flanking regions. Such sequences are usually obtained either from the mammary-gland specific gene from which the promoter and enhancer are obtained or from the lysosomal protein gene being expressed. Inclusion of such sequences produces a genetic milieu simulating that of an authentic mammary gland specific gene and/or that of an authentic lysosomal protein gene. This genetic milieu results in some cases (e.g., bovine αS1-casein) in higher expression of the transcribed gene. Alternatively, 3' flanking regions and untranslated regions are obtained from other heterologous genes such as the P-globin gene or viral genes. The inclusion of 3' and 5' untranslated regions from a lysosomal protein gene, or other heterologous gene can also increase the stability of the transcript.

In some embodiments, about 0.5, 1, 5, 10, 15, 20 or 30 kb of 5' flanking sequence is included from a mammary specific gene in combination with about 1, 5, 10, 15, 20 or 30 kb or 3' flanking sequence from the lysosomal protein gene being expressed. If the protein is expressed from a cDNA sequence, it is advantageous to include an intronic sequence between the promoter and the coding sequence. The intronic sequence is preferably a hybrid sequence formed from a 5' portion from an intervening sequence from the first intron of the mammary gland specific region from which the promoter is obtained and a 3' portion from an intervening sequence of an IgG intervening sequence or lysosomal protein gene. See DeBoer et al., WO 91/08216 (incorporated by reference in its entirety for all purposes).

A preferred transgene for expressing a lysosomal protein comprises a cDNA-genomic hybrid lysosomal protein gene-linked 5' to a casein promoter and enhancer. The hybrid gene includes the signal sequence, coding region, and a 3' flanking region from the lysosomal protein gene. Optionally, the cDNA segment includes an intronic sequence between the 5' casein and untranslated region of the gene encoding the lysosomal protein. Of course, corresponding cDNA and genomic segments can also be fused at other locations within the gene provided a contiguous protein can be expressed from the resulting fusion.

Other preferred transgenes have a genomic lysosomal protein segment linked 5' to casein regulatory sequences. The genomic segment is usually contiguous from the 5' untranslated region to the 3' flanking region of the gene. Thus, the genomic segment includes a portion of the lysosomal protein 5' untranslated sequence, the signal sequence, alternating introns and coding exons, a 3' untranslated region, and a 3' flanking region. The genomic segment is linked via the 5' untranslated region to a casein fragment comprising a promoter and enhancer and usually a 5' untranslated region.

DNA sequence information is available for all of the mammary gland specific genes listed above, in at least one, and often several organisms. See, e.g., Richards et al., J. Biol. Chem. 256, 526-532 (1981) (α-lactalbumin rat); Campbell et al., Nucleic Acids Res. 12, 8685-8697 (1984) (rat WAP); Jones et al., J. Biol. Chem. 260, 7042-7050 (1985)) (rat. β-casein); Yu-Lee and Rosen, J. Biol. Chem. 258, 10794-10804 (1983) (rat γ casein)); Hall, Biochem. J. 242, 735-742 (1987) (α-lactalbumin human); Stewart, Nucleic Acids Res. 12, 389 (1984) (bovine αs1 and K casein cDNAs); Gorodetsky et al., Gene 66, 87-96 (1988) (bovine β casein); Alexander et al., Eur. J. Biochem. 178, 395-401 (1988) (bovine κ casein); Brignon et al., FEBS Lett. 188, 48-55 (1977) (bovine αS2 casein); Jamieson et al., Gene 61, 85-90 (1987), Ivanov et al., Biol. Chem. Hoppe-Seyler 369, 425-429 (1988), Alexander et al., Nucleic Acids Res. 17, 6739 (1989) (bovine β lactoglobulin); Vilotte et al., Biochimie 69, 609-620 (1987) (bovine α-lactalbumin) (incorporated by reference in their entirety for all purposes). The structure and function of the various milk protein genes are reviewed by Mercier and Vilotte, J. Dairy Sci. 76, 3079-3098 (1993) (incorporated by reference in its entirety for all purposes). To the extent that additional sequence data might be required, sequences flanking the regions already obtained could be readily cloned using the existing sequences as probes. Mammary-gland specific regulatory sequences from different organisms are likewise obtained by screening libraries from such organisms using known cognate nucleotide sequences, or antibodies to cognate proteins as probes.

General strategies and exemplary transgenes employing αS1-casein regulatory sequences for targeting the expression of a recombinant protein to the mammary gland are described in more detail in DeBoer et al., WO 91/08216 and WO 93/25567 (incorporated by reference in their entirety for all purposes). Examples of transgenes employing regulatory sequences from other mammary gland specific genes have also been described. See, e.g., Simon et al., Bio/Technology 6, 179-183 (1988) and WO88/00239 (1988) (β-lactoglobulin regulatory sequence for expression in sheep); Rosen, EP 279, 582 and Lee et al., Nucleic Acids Res. 16, 1027-1041 (1988) (β-casein regulatory sequence for expression in mice); Gordon, Biotechnology 5, 1183 (1987) (WAP regulatory sequence for expression in mice); WO 88/01648 (1988) and Eur. J. Biochem. 186, 43-48 (1989) (α-lactalbumin regulatory sequence for expression in mice) (incorporated by reference in their entirety for all purposes).

The expression of lysosomal proteins in the milk from transgenes can be influenced by co-expression or functional inactivation (i.e., knock-out) of genes involved in post translational modification and targeting of the lysosomal proteins. The data in the Examples indicate that surprisingly mammary glands already express modifying enzymes at sufficient quantities to obtain assembly and secretion of mannose 6-phosphate containing proteins at high levels. However, in some transgenic mammals expressing these proteins at high levels, it is sometimes preferable to supplement endogenous levels of processing enzymes with additional enzyme resulting from transgene expression. Such transgenes are constructed employing similar principles to those discussed above with the processing enzyme coding sequence replacing the lysosomal protein coding sequence in the transgene. It is not generally necessary that posttranslational processing enzymes be secreted. Thus, the secretion signal sequence linked to the lysosomal protein coding sequence is replaced with a signal sequence that targets the processing enzyme to the endoplasmic reticulum without secretion. For example, the signal sequences naturally associated with these enzymes are suitable.

D. Transgenesis

The transgenes described above are introduced into nonhuman mammals. Most nonhuman mammals, including rodents such as mice and rats, rabbits, ovines such as sheep and goats, porcines such as pigs, and bovines such as cattle and buffalo, are suitable. Bovines offer an advantage of large yields of milk, whereas mice offer advantages of ease of transgenesis and breeding. Rabbits offer a compromise of these advantages. A rabbit can yield 100 ml milk per day with a protein content of about 14% (see Buhler et al., Biotechnology 8, 140 (1990)) (incorporated by reference in its entirety for all purposes), and yet can be manipulated and bred using the same principles and with similar facility as mice. Nonviviparous mammals such as a spiny anteater or duckbill platypus are typically not employed.

In some methods of transgenesis, transgenes are introduced into the pronuclei of fertilized oocytes. For some animals, such as mice and rabbits, fertilization is performed in vivo and fertilized ova are surgically removed. In other animals, particularly bovines, it is preferable to remove ova from live or slaughterhouse animals and fertilize the ova in vitro. See DeBoer et al., WO 91/08216. In vitro fertilization permits a transgene to be introduced into substantially synchronous cells at an optimal phase of the cell cycle for integration (not later than S-phase). Transgenes are usually introduced by microinjection. See U.S. Pat. No. 4,873,292. Fertilized oocytes are then cultured in vitro until a pre-implantation embryo is obtained containing about 16-150 cells. The 16-32 cell stage of an embryo is described as a morula. Pre-implantation embryos containing more than 32 cells are termed blastocysts. These embryos show the development of a blastocoele cavity, typically at the 64 cell stage. Methods for culturing fertilized oocytes to the pre-implantation stage are described by Gordon et al., Methods Enzymol. 101, 414 (1984); Hogan et al., Manipulation of the Mouse Embryo: A Laboratory Manual, C.S.H.L. N.Y. (1986) (mouse embryo); and Hammer et al., Nature 315, 680 (1985) (rabbit and porcine embryos); Gandolfi et al. J. Reprod. Fert. 81, 23-28 (1987); Rexroad et al., J. Anim. Sci. 66, 947-953 (1988) (ovine embryos) and Eyestone et al. J. Reprod. Fert. 85, 715-720 (1989); Camous et al., J. Reprod. Fert. 72, 779-785 (1984); and Heyman et al. Theriogenology 27, 5968 (1987) (bovine embryos) (incorporated by reference in their entirety for all purposes). Sometimes pre-implantation embryos are stored frozen for a period pending implantation. Pre-implantation embryos are transferred to the oviduct of a pseudopregnant female resulting in the birth of a transgenic or chimeric animal depending upon the stage of development when the transgene is integrated. Chimeric mammals can be bred to form true germline transgenic animals.

Alternatively, transgenes can be introduced into embryonic stem cells (ES). These cells are obtained from preimplantation embryos cultured in vitro. Bradley et al., Nature 309, 255-258 (1984) (incorporated by reference in its entirety for all purposes). Transgenes can be introduced into such cells by electroporation or microinjection. Transformed ES cells are combined with blastocysts from a non-human animal. The ES cells colonize the embryo and in some embryos form the germline of the resulting chimeric animal. See Jaenisch, Science, 240, 1468-1474 (1988) (incorporated by reference in its entirety for all purposes). Alternatively, ES cells can be used as a source of nuclei for transplantation into an enucleated fertilized oocyte giving rise to a transgenic mammal.

For production of transgenic animals containing two or more transgenes, the transgenes can be introduced simultaneously using the same procedure as for a single transgene. Alternatively, the transgenes can be initially introduced into separate animals and then combined into the same genome by breeding the animals. Alternatively, a first transgenic animal is produced containing one of the transgenes. A second transgene is then introduced into fertilized ova or embryonic stem cells from that animal. In some embodiments, transgenes whose length would otherwise exceed about 50 kb, are constructed as overlapping fragments. Such overlapping fragments are introduced into a fertilized oocyte or embryonic stem cell simultaneously and undergo homologous recombination in vivo. See Kay et al., WO 92/03917 (incorporated by reference in its entirety for all purposes).

E. Characteristics of Transgenic Mammals

Transgenic mammals of the invention incorporate at least one transgene in their genome as described above. The transgene targets expression of a DNA segment encoding a lysosomal protein at least predominantly to the mammary gland. Surprisingly, the mammary glands are capable of expressing proteins required for authentic posttranslation processing including steps of oligosaccharide addition and phosphorylation. Processing by enzymes in the mammary gland results in phosphorylation of the 6' position of mannose groups.

Lysosomal proteins can be secreted at high levels of at least 10, 50, 100, 500, 1000, 2000, 5000 or 10,000 .µg/ml. Surprisingly, the transgenic mammals of the invention exhibit substantially normal health. Secondary expression of lysosomal proteins in tissues other than the mammary gland does not occur to an extent sufficient to cause deleterious effects. Moreover, exogenous lysosomal protein produced in the mammary gland is secreted with sufficient efficiency that no significant problem is presented by deposits clogging the secretory apparatus.

The age at which transgenic mammals can begin producing milk, of course, varies with the nature of the animal. For transgenic bovines, the age is about two-and-a-half years naturally or six months with hormonal stimulation, whereas for transgenic mice the age is about 5-6 weeks. Of course, only the female members of a species are useful for producing milk. However, transgenic males are also of value for breeding female descendants. The sperm from transgenic males can be stored frozen for subsequent in vitro fertilization and generation of female offspring F. Recovery of Proteins from Milk Transgenic adult female mammals produce milk containing high concentrations of exogenous lysosomal protein. The protein can be purified from milk, if desired, by virtue of its distinguishing physical and chemical properties, and standard purification procedures such as precipitation, ion exchange, molecular exclusion or affinity chromatography. See generally Scopes, Protein Purification (Springer-Verlag, N.Y., 1982).

Purification of human acid α-glucosidase from milk can be carried out by defatting of the transgenic milk by centrifugation and removal of the fat, followed by removal of caseins by high speed centrifugation followed by dead-end filtration (i.e., dead-end filtration by using successively declining filter sizes) or cross-flow filtration, or; removal of caseins directly by cross-flow filtration. Human acid α-glucosidase is purified by chromatography, including Q Sepharose FF (or other anion-exchange matrix), hydrophobic interaction chromatography (HIC), metal-chelating Sepharose, or lectins coupled to Sepharose (or other matrices).

Q Sepharose Fast Flow chromatography may be used to purify human acid α-glucosidase present in filtered whey or whey fraction as follows: a Q Sepharose Fast Flow (QFF; Pharmacia) chromatography (Pharmacia XK-50 column, 15 cm bed height; 250 cm/hr flow rate) the column was equilibrated in 20 mM sodium phosphate buffer, pH 7.0 (buffer A); the S/D-incubated whey fraction (about 500 to 600 ml) is loaded and the column is washed with 4-6 column volumes (cv) of buffer A (20 mM sodium phosphate buffer, pH 7.0). The human acid α-glucosidase fraction is eluted from the Q FF column with 2-3 cv buffer A, containing 100 mM NaCl.

The Q FF Sepharose human acid α-glucosidase containing fraction can be further purified using Phenyl Sepharose High Performance chromatography. For example, 1 vol. of 1 M ammonium sulphate is added to the Q FF Sepharose human acid α-glucosidase eluate while stirring continuously. Phenyl HP (Pharmacia) column chromatography (Pharmacia XK-50 column, 15 cm bed height; 150 cm/hr flow rate) is then done at room temperature by equilibrating the column in 0.5 M ammonium sulphate, 50 mM sodium phosphate buffer pH 6.0 (buffer C), loading the 0.5 M ammoniumsulphate-incubated human acid α-glucosidase eluate (from Q FF Sepharose), washing the column with 24 cv of buffer C, and eluting the human acid α-glucosidase was eluted from the Phenyl HP column with 3-5 cv buffer D (50 mM sodium phosphate buffer at pH 6.0). Alternative methods and additional methods for further purifying human acid α-glucosidase will be apparent to those of skill. For example, see United Kingdom patent application 998 07464.4 (incorporated by reference in its entirety for all purposes).

G. Uses of Recombinant Lysosomal Proteins

The recombinant lysosomal proteins produced according to the invention find use in enzyme replacement therapeutic procedures. A patient having a genetic or other deficiency resulting in an insufficiency of a functional lysosomal enzyme can be treated by administering exogenous enzyme to the patient. Patients in need of such treatment can be identified from symptoms (e.g., Hurler's syndrome symptoms include Dwarfism, corneal clouding, hepatosplenomegaly, valvular lesions, coronary artery lesions, skeletal deformities, joint stiffness and progressive mental retardation). Alternatively, or additionally, patients can be diagnosed from biochemical analysis of a tissue sample to reveal excessive accumulation of a characteristic metabolite processed by a particular lysosomal enzyme or by enzyme assay using an artificial or natural substrate to reveal deficiency of a particular lysosomal enzyme activity. For most diseases, diagnosis can be made by measuring the particular enzyme deficiency or by DNA analysis before occurrence of symptoms or excessive accumulation of metabolites (Scriver et al., supra, chapters on lysosomal storage disorders). All of the lysosomal storage diseases are hereditary. Thus, in offspring from families known to have members suffering from lysosomal diseases, it is sometimes advisable to commence prophylactic treatment even before a definitive diagnosis can be made.

Pharmaceutical Compositions

In some methods, lysosomal enzymes are administered in purified form together with a pharmaceutical carrier as a pharmaceutical composition. The preferred form depends on the intended mode of administration and therapeutic application. The pharmaceutical carrier can be any compatible, non-toxic substance suitable to deliver the polypeptides to the patient. Sterile water, alcohol, fats, waxes, and inert solids may be used as the carrier. Pharmaceutically-acceptable adjuvants, buffering agents, dispersing agents, and the like, may also be incorporated into the pharmaceutical compositions.

The concentration of the enzyme in the pharmaceutical composition can vary widely, i.e., from less than about 0.1% by weight, usually being at least about 1% by weight to as much as 20% by weight or more.

For oral administration, the active ingredient can be administered in solid dosage forms, such as capsules, tablets, and powders, or in liquid dosage forms, such as elixirs, syrups, and suspensions. Active component(s) can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate and the like. Examples of additional inactive ingredients that may be added to provide desirable color, taste, stability, buffering capacity, dispersion or other known desirable features are red iron oxide, silica gel, sodium lauryl sulfate, titanium dioxide, edible white ink and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

A typical composition for intravenous infusion could be made up to contain 100 to 500 ml of sterile 0.9% NaCl or 5% glucose optionally supplemented with a 20% albumin solution and 100 to 500 mg of an enzyme. A typical pharmaceutical compositions for intramuscular injection would be made up to contain, for example, 1 ml of sterile buffered water and 1 to 10 mg of the purified alpha glucosidase of the present invention. Methods for preparing parenterally administrable compositions are well known in the art and described in more detail in various sources, including, for example, Remington's Pharmaceutical Science (15th ed., Mack Publishing, Easton, Pa., 1980) (incorporated by reference in its entirety for all purposes).

AGLU can be formulated in 10 mM sodium phosphate buffer pH 7.0. Small amounts of ammonium sulphate are optionally present (<10 mM). The enzyme is typically kept frozen at about −70.degree. C., and thawed before use. Alternatively, the enzyme may be stored cold (e.g., at about 4.degree. C. to 8.degree. C.) in solution. In some embodiments, AGLU solutions comprise a buffer (e.g., sodium phosphate, potassium phosphate or other physiologically acceptable buffers), a simple carbohydrate (e.g., sucrose, glucose, maltose, mannitol or the like), proteins (e.g., human serum albumin), and/or surfactants (e.g., polysorbate 80 (Tween-80), cremophore-EL, cremophore-R, labrofil, and the like).

AGLU can also be stored in lyophilized form. For lyophilization, AGLU can be formulated in a solution containing mannitol, and sucrose in a phosphate buffer. The concentration of sucrose should be sufficient to prevent aggregation of AGLU on reconstitution. The concentration of mannitol should be sufficient to significantly reduce the time otherwise needed for lyophilization. The concentrations of mannitol and sucrose should, however, be insufficient to cause unacceptable hypertonicity on reconstitution. Concentrations of mannitol and sucrose of 1-3 mg/ml and 0.1-1.0 mg/ml respectively are suitable. Preferred concentrations are 2 mg/ml mannitol and 0.5 mg/ml sucrose. AGLU is preferably at 5 mg/ml before lyophilization and after reconstitution. Saline preferably at 0.9% is a preferred solution for reconstitution.

For AGLU purified from rabbit milk, a small amount of impurities (e.g., up to about 5%/o) can be tolerated. Possible impurities may be present in the form of rabbit whey proteins. Other possible impurities are structural analogues (e.g., oligomers and aggregates) and truncations of AGLU. Current batches indicate that the AGLU produced in transgenic rabbits is >95% pure. The largest impurities are rabbit whey proteins, although on gel electrophoresis, AGLU bands of differing molecular weights are also seen.

Infusion solutions should be prepared aseptically in a laminar air flow hood. The appropriate amount of AGLU should be removed from the freezer and thawed at room temperature. Infusion solutions can be prepared in glass infusion bottles by mixing the appropriate amount of AGLU finished product solution with an adequate amount of a solution containing human serum albumin (HSA) and glucose. The final concentrations can be 1% HSA and 4% glucose for 25-200 mg doses and 1% HSA and 4% glucose for 400-800 mg doses. HSA and AGLU can be filtered with a 0.2 .µm syringe filter before transfer into the infusion bottle containing 5% glucose. Alternatively, AGLU can be reconstituted in saline solution, preferably 0.9% for infusion. Solutions of AGLU for infusion have been shown to be stable for up to 7 hours at room temperature. Therefore the AGLU solution is preferably infused within seven hours of preparation.

Therapeutic Methods

The present invention provides effective methods of treating Pompe's disease. These methods are premised in part on the availability of large amounts of human acid alpha glucosidase in a form that is catalytically active and in a form that can be taken up by tissues, particularly, liver, heart and muscle (e.g., smooth muscle, striated muscle, and cardiac muscle), of a patient being treated. Such human acid alpha-glucosidase is provided from e.g., the transgenic animals described in the Examples. The alpha-glucosidase is preferably predominantly (i.e., >50%) in the precursor form of about 100-110 kD. (The apparent molecular weight or relative mobility of the 100-110 kD precursor may vary somewhat depending on the method of analysis used, but is typically within the range 95 kD and 120 kD.) Given the successful results with human acid alpha-glucosidase in the transgenic animals discussed in the Examples, it is possible that other sources of human alpha-glucosidase, such as resulting from cellular expression systems, can also be used. For example, an alternative way to produce human acid α-glucosidase is to transfect the acid α-glucosidase gene into a stable eukaryotic cell line (e.g., CHO) as a cDNA or genomic construct operably linked to a suitable promoter. However, it is more laborious to produce the large amounts of human acid alpha glucosidase needed for clinical therapy by such an approach.

The pharmaceutical compositions of the present invention are usually administered intravenously. Intradermal, intramuscular or oral administration is also possible in some circumstances. The compositions can be administered for prophylactic treatment of individuals suffering from, or at risk of, a lysosomal enzyme deficiency disease. For therapeutic applications, the pharmaceutical compositions are administered to a patient suffering from established disease in an amount sufficient to reduce the concentration of accumulated metabolite and/or prevent or arrest further accumulation of metabolite. For individuals at risk of lysosomal enzyme deficiency disease, the pharmaceutical compositions are administered prophylactically in an amount sufficient to either prevent or inhibit accumulation of metabolite. An amount adequate to accomplish this is defined as a "therapeutically-" or "prophylactically-effective dose." Such effective dosages will depend on the severity of the condition and on the general state of the patient's health.

In the present methods, human acid alpha glucosidase is usually administered at a dosage of 10 mg/kg patient body weight or more per week to a patient. Often dosages are greater than 10 mg/kg per week. Dosages regimes can range from 10 mg/kg per week to at least 1000 mg/kg per week. Typically dosage regimes are 10 mg/kg per week, 15 mg/kg per week, 20 mg/kg per week, 25 mg/kg per week, 30 mg/kg per week, 35 mg/kg per week, 40 mg/kg week, 45 mg/kg per week, 60 mg/kg week, 80 mg/kg per week and 120 mg/kg per week. In preferred regimes 10 mg/kg, 15 mg/kg, 20 mg/kg, 30 mg/kg or 40 mg/kg is administered once, twice or three times weekly. Treatment is typically continued for at least 4 weeks, sometimes 24 weeks, and sometimes for the life of the patient. Treatment is preferably administered i.v. Optionally, levels of human alpha-glucosidase are monitored following treatment (e.g., in the plasma or muscle) and a further dosage is administered when detected levels fall substantially below (e.g., less than 20%) of values in normal persons.

In some methods, human acid alpha glucosidase is administered at an initially "high" dose (i.e., a "loading dose"), followed by administration of a lower doses (i.e., a "maintenance dose"). An example of a loading dose is at least about 40 mg/kg patient body weight 1 to 3 times per week (e.g., for 1, 2, or 3 weeks). An example of a maintenance dose is at least about 5 to at least about 10 mg/kg patient body weight per week, or more, such as 20 mg/kg per week, 30 mg/kg per week, 40 mg/kg week.

In some methods, a dosage is administered at increasing rate during the dosage period. Such can be achieved by increasing the rate of flow intravenous infusion or by using a gradient of increasing concentration of alpha-glucosidase administered at constant rate. Administration in this manner reduces the risk of immunogenic reaction. In some dosages, the rate of administration measured in units of alpha glucosidase per unit time increases by at least a factor of ten. Typically, the intravenous infusion occurs over a period of several hours (e.g., 1-10 hours and preferably 2-8 hours, more preferably 3-6 hours), and the rate of infusion is increased at intervals during the period of administration.

Suitable dosages (all in mg/kg/hr) for infusion at increasing rates are shown in table 1 below. The first column of the table indicates periods of time in the dosing schedule. For example, the reference to 0-1 hr refers to the first hour of the dosing. The fifth column of the table shows the range of doses than can be used at each time period. The fourth column shows a narrower included range of preferred dosages. The third column indicates upper and lower values of dosages administered in an exemplary clinical trial. The second column shows particularly preferred dosages, these representing the mean of the range shown in the third column of table 1.

TABLE 1

| Time | Mean Doses (I) | Lower&Upper Values | Preferred Range | Range |
| --- | --- | --- | --- | --- |
| 0-1 hr: | 0.3 mg/kg/hr | 0.25-0.4 | 0.1-1 | 0.03-3 |
| 1-2 hr: | 1 mg/kg/hr | 0.9-1.4 | 1-4 | 0.3-12 |
| 2.2.5 hr: | 4 mg/kg/hr | 3.6-5.7 | 3-10 | 1-30 |
| 2.5-5.6 hr: | 12 mg/kg/hr | 7.2-11.3 | 6-20 | 2.60 |

The methods are effective on patients with both early onset (infantile) and late onset (juvenile and adult) Pompe's disease. In patients with the infantile form of Pompe's disease symptoms become apparent within the first 4 months of life. Mostly, poor motor development and failure to thrive are noticed first. On clinical examination, there is generalized hypotonia with muscle wasting, increased respiration rate with sternal retractions, moderate enlargement of the liver, and protrusion of the tongue. Ultrasound examination of the heart shows a progressive hypertrophic cardiomyopathy, eventually leading to insufficient cardiac output. The ECG is characterized by marked left axis deviation, a short PR interval, large QRS complexes, inverted T waves and ST depression. The disease shows a rapidly progressive course leading to cardiorespiratory failure within the first year of life. On histological examination at autopsy lysosomal glycogen storage is observed in various tissues, and is most pronounced in heart and skeletal muscle. Treatment with human acid alpha glucosidase in the present methods results in a prolongation of life of such patients (e.g., greater than 1, 2, 5 years up to a normal lifespan). Treatment can also result in elimination or reduction of clinical and biochemical characteristics of Pompe's disease as discussed above. Treatment is administered soon after birth, or antenatally if the parents are known to bear variant alpha glucosidase alleles placing their progeny at risk.

Patients with the late onset adult form of Pompe's disease may not experience symptoms within the first two decades of life. In this clinical subtype, predominantly skeletal muscles are involved with predilection of those of the limb girdle, the trunk and the diaphragm. Difficulty in climbing stairs is often the initial complaint. The respiratory impairment varies considerably. It can dominate the clinical picture, or it is not experienced by the patient until late in life. Most such patients die because of respiratory insufficiency. In patients with the juvenile subtype, symptoms usually become apparent in the first decade of life. As in adult Pompe's disease, skeletal muscle weakness is the major problem; cardiomegaly, hepatomegaly, and macroglossia can be seen, but are rare. In many cases, nightly ventilatory support is ultimately needed. Pulmonary infections in combination with wasting of the respiratory muscles are life threatening and mostly become fatal before the third decade. Treatment with the present methods prolongs the life of patients with late onset juvenile or adult Pompe's disease up to a normal life span. Treatment also eliminates or significantly reduces clinical and biochemical symptoms of disease.

Other Uses

Lysosomal proteins produced in the milk of transgenic animals have a number of other uses. For example, α-glucosidase, in common with other α-amylases, is an important tool in production of starch, beer and pharmaceuticals. See. Vihinen and Mantsala, Crit. Rev. Biochem. Mol. Biol. 24, 329-401 (1989) (incorporated by reference in its entirety for all purpose). Lysosomal proteins are also useful for producing laboratory chemicals or food products. For example, acid α-glucosidase degrades 1,4 and 1,6 α-glucidic bonds and can be used for the degradation of various carbohydrates containing these bonds, such as maltose, isomaltose, starch and glycogen, to yield glucose. Acid α-glucosidase is also useful for administration to patients with an intestinal maltase or isomaltase deficiency. Symptoms otherwise resulting from the presence of undigested maltose are avoided. In such applications, the enzyme can be administered without prior fractionation from milk, as a food product derived from such milk (e.g., ice cream or cheese) or as a pharmaceutical composition. Purified recombinant lysosomal enzymes are also useful for inclusion as controls in diagnostic kits for assay of unknown quantities of such enzymes in tissue samples.

EXAMPLES

Example 1

Construction of Transgenes (a) cDNA Construct

Construction of an expression vector containing cDNA encoding human acid α-glucosidase started with the plasmid p16,8hlf3 (see DeBoer et al. (1991) and (1993), supra) This plasmid includes bovine αS1-casein regulatory sequences. The lactoferrin cDNA insert of the parent plasmid was exchanged for the human acid α-glucosidase cDNA (Hoefsloot et al. EMBO J. 7, 1697-1704 (1988)) at the ClaI site and SalI site of the expression cassette as shown in FIG. 1. To obtain the compatible restriction sites at the ends of the α-glucosidase cDNA fragment, plasmid pSHAG2 (id.) containing the complete cDNA encoding human α-glucosidase was digested with EcoRI and SphI and the 3.3 kb cDNA-fragment was subcloned in pKUN7ΔC, a pKUN1 derivative (Konings et al., Gene 46, 269-276 (1986)), with a destroyed ClaI site within the vector nucleotide sequences and with a newly designed polylinker: HindIII ClaI EcoRI SphI XhoI EcoRI SfiI SfiI/SmaI NotI EcoRI* (*=destroyed site). From the resulting plasmid pagluCESX, the 3.3-kb cDNA-fragment could be excised by ClaI and XhoI. This fragment was inserted into the expression cassette shown in FIG. 1 at the ClaI site and XhoI-compatible SalI site. As a result, the expression plasmid p16,8αglu consists of the cDNA sequence encoding human acid α-glucosidase flanked by bovine αS1 casein sequences as shown in FIG. 1. The 27.3-kb fragment containing the complete expression cassette can be excised by cleavage with NotI (see FIG. 1).

(b) Genomic Constructs

Construct c8αgluex1 contains the human acid α-glucosidase gene (Hoefsloot et al., Biochem. J. 272, 493-497 (1990)); starting in exon 1 just downstream of its transcription initiation site (see FIG. 2, panel A). Therefore, the construct encodes almost a complete 5' UTR of the human acid α-glucosidase gene. This fragment was fused to the promoter sequences of the bovine αS1-casein gene. The αS1-casein initiation site is present 22 bp upstream of the αS1-casein/ acid α-glucosidase junction. The construct has the human acid α-glucosidase polyadenylation signal and 3' flanking sequences. Construct c8αgluex2 contains the bovine αS1-casein promoter immediately fused to the translation initiation site in exon 2 of the human acid α-glucosidase gene (see FIG. 2, panel B). Thus, the αS1-casein transcription initiation site and the α-glucosidase translation initiation site are 22-bp apart in this construct. Therefore no α-glucosidase 5' UTR is preserved. This construct also contains the human acid α-glucosidase polyadenylation signal and 3' flanking sequences as shown in FIG. 2, panel B.

Construct c8,8αgluex2-20 differs from construct c8αgluex2 only in the 3' region. A SphI site in exon 20 was used to fuse the bovine αS1-casein 3' sequence to the human acid α-glucosidase construct. The polyadenylation signal is located in this 3' αS1-casein sequence (FIG. 2, panel C).

Construct c8,8αgluex2-20 differs from construct c8αgluex2 only in the 3' region. A SphI site in exon 20 was used to fuse the bovine αS1-casein 3' sequence to the human acid α-glucosidase construct. The polyadenylation signal is located in this 3' αS1 casein sequence (FIG. 2, panel C).

Methods for Construction of Genomic Constructs

Three contiguous BglII fragments containing the human acid α-glucosidase gene were isolated by Hoefsloot et al., supra. These fragments were ligated in the BglII-site of pKUN8ΔC, a pKUN7ΔC derivative with a customized polylinker: HindIII ClaI StuI SstI BglII PvnI NcoI EcoRI SphI XhoI EcoRI* SmaI/SfiI NotI EcoRI* (*=destroyed site). This ligation resulted in two orientations of the fragments generating plasmids p7.3αgluBES, p7.3αgluBSE, p8.5αgluBSE, p8.5αgluBES, p10αgluBSE and p10αgluBES.

Because unique NotI-sites at the ends of the expression cassette are used subsequently for the isolation of the fragments used for microinjection, the intragenic NotI site in intron 17 of human acid α-glucosidase had to be destroyed. Therefore, p10αgluBES was digested with ClaI and XhoI; the fragment containing the 3' α-glucosidase end was isolated. This fragment was inserted in the ClaI and XhoI sites of pKUN10ΔC, resulting in p10αgluNV. Previously pKUN10ΔC (i.e., a derivative of pKUN8ΔC) was obtained by digesting pKUN8ΔC with NotI, filling in the sticky ends with Klenow and subsequently, annealing the plasmid by blunt-ended ligation. Finally, p10αgluΔNV was digested with NotI. These sticky ends were also filled with Klenow and the fragment was ligated, resulting in plasmid p10αgluΔNotI.

Construction of c8αgluex1

Since the SstI site in first exon of the α-glucosidase gene was chosen for the fusion to the bovine αS1-casein sequence, p8.5αgluBSE was digested with BglII followed by a partial digestion with SstI. The fragment containing exon 1-3 was isolated and ligated into the BglII and SstI sites of pKUN8ΔC. The resulting plasmid was named: p5'αgluex1. (see FIG. 3, panel A).

The next step (FIG. 3, panel B) was the ligation of the 3' part to p5'αgluex1. First, p10αgluΔN was digested with BglII and BamHI. This fragment containing exon 16-20 was isolated. Second, p5'αgluex1 was digested with BglII and to prevent self-ligation, and treated with phosphorylase (BAP) to dephosphorylate the sticky BglII ends. Since BamHI sticky ends are compatible with the BglII sticky ends, these ends ligate to each other. The resulting plasmid, i.e., p5'3'αgluex1, was selected. This plasmid has a unique BglII site available for the final construction step (see FIG. 3, panels B and C).

Figure 3A:
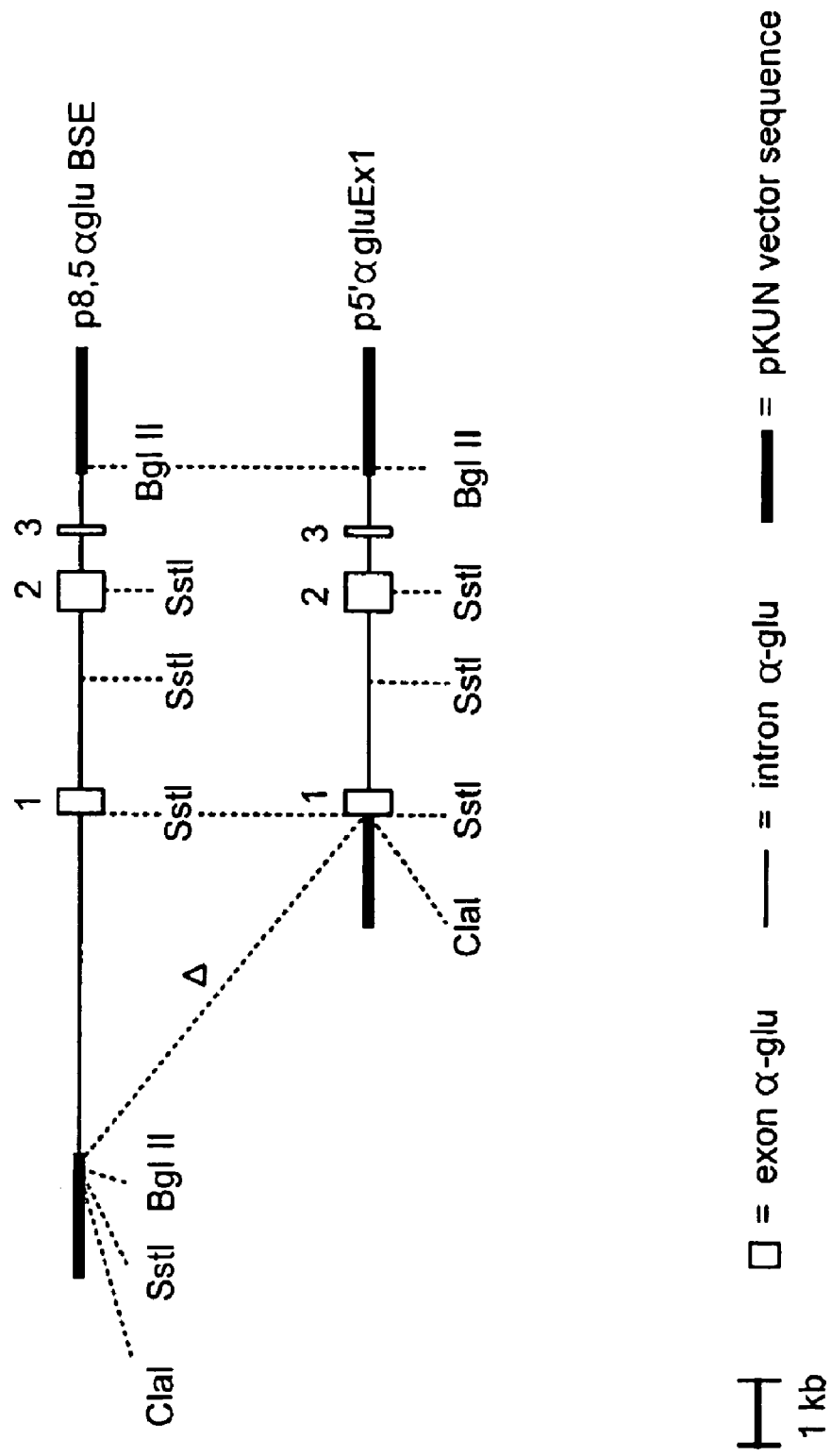
FIG. 3 (panels A, B, C): Construction of genomic transgenes. The α-glucosidase exons are represented by open boxes; the α-glucosidase introns and nontranslated sequences are indicated by thin lines. The pKUN vector sequences are represented by thick lines.
Figure 3B:
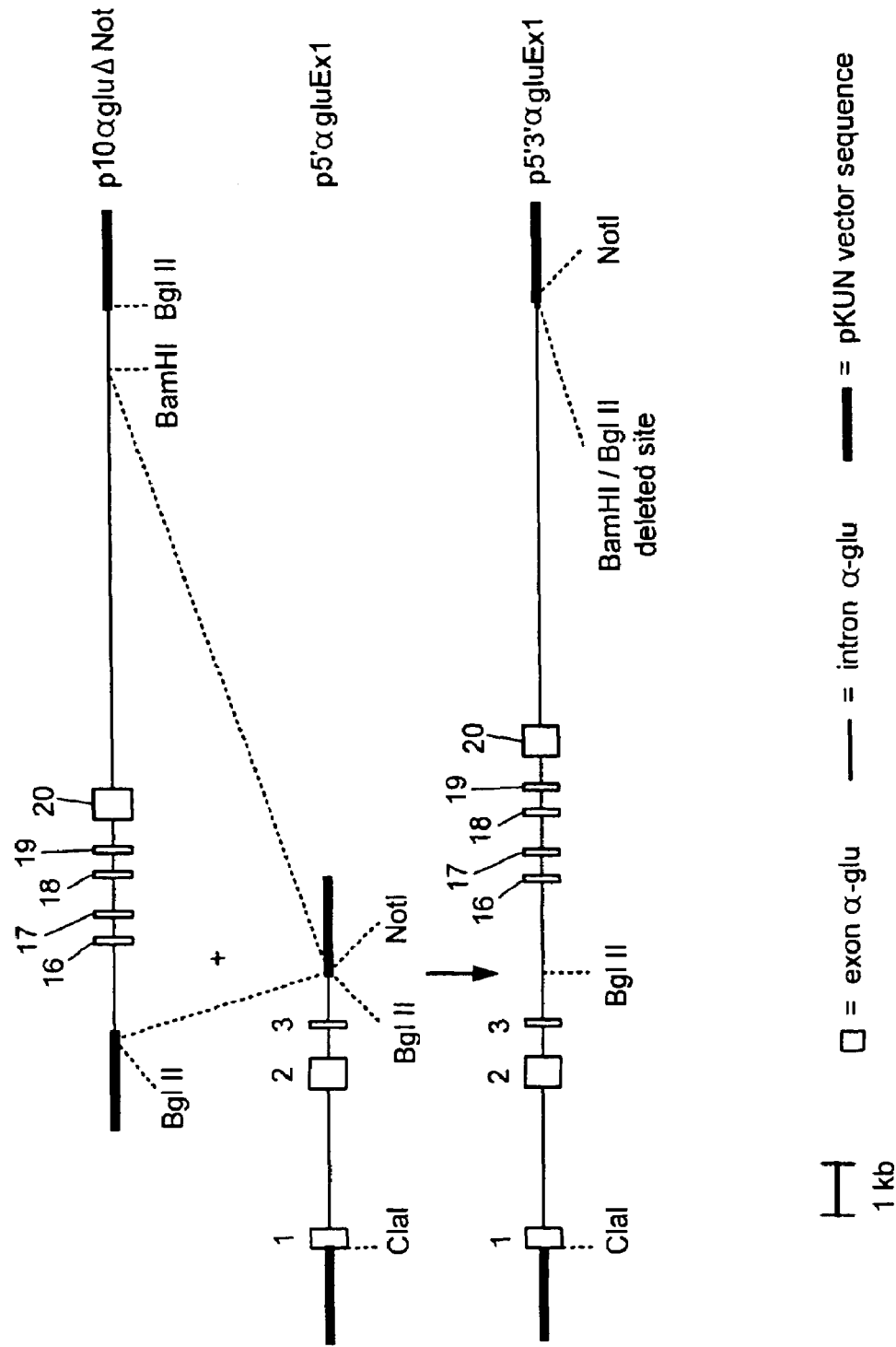
Figure 3C:
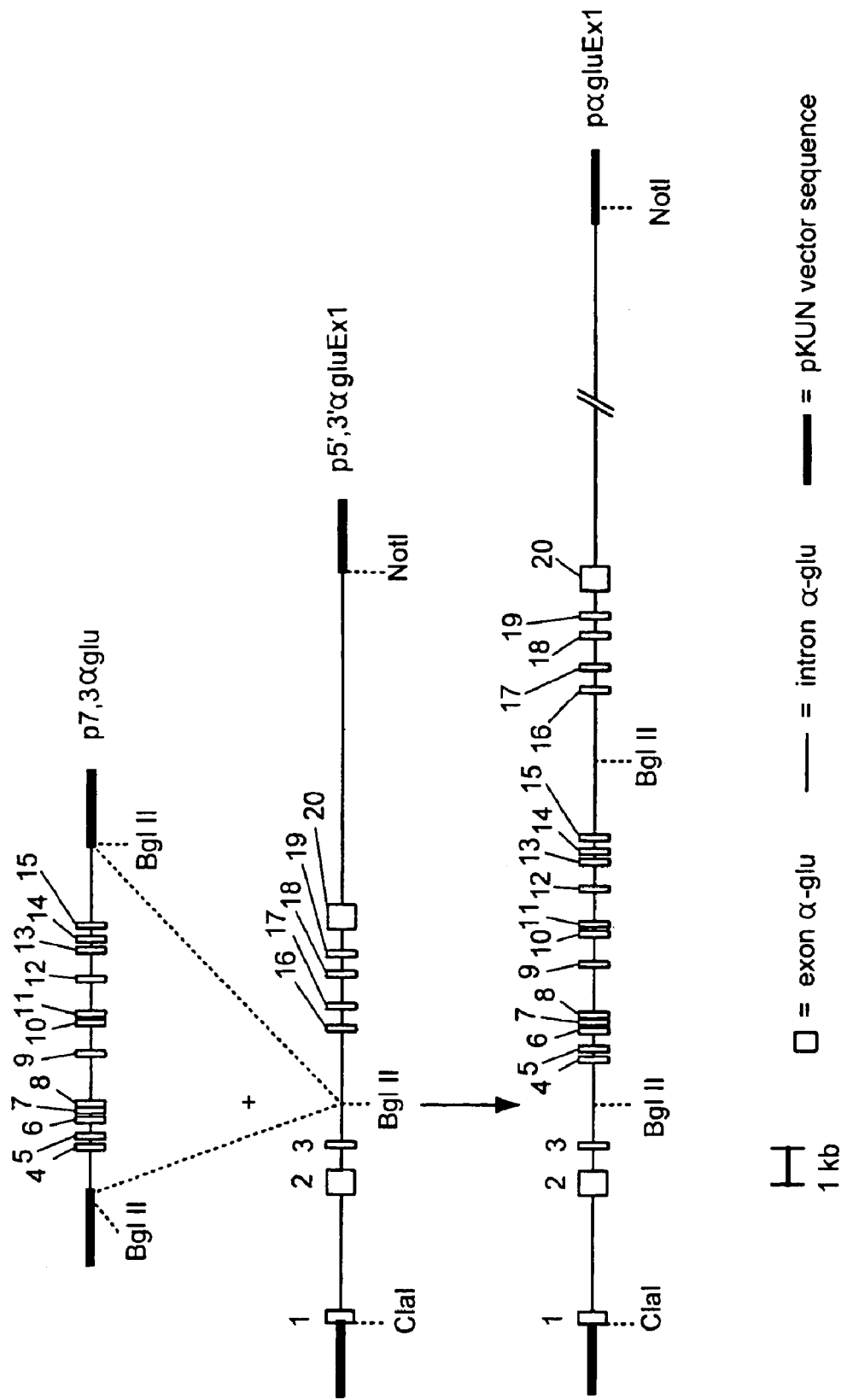

The middle part of the α-glucosidase gene was inserted into the latter construct. For this step, p7.3αgluBSE was digested with BglII, the 8.5-kb fragment was isolated and ligated to the BglII digested and dephosphorylated p5'3'αgluex1 plasmid. The resulting plasmid is pαgluex1 (FIG. 3, panel C).

The bovine αS1-casein promoter sequences were incorporated in the next step via a ligation involving three fragments. The pWE15 cosmid vector was digested with NotI and dephosphorylated. The bovine αS1-casein promoter was isolated as an 8 Rb NotI-ClaI fragment (see de Boer et al., 1991, supra). The human acid α-glucosidase fragment was isolated from pαgluex1 using the same enzymes. These three fragments were ligated and packaged using the Stratagene Gigapack II kit in 1046 E. coli host cells. The resulting cosmid c8αgluex1 was propagated in E. coli strain DH5α. The vector was linearized with NotI before microinjection.

Construction of c8αgluex2 and c8.8αgluex2-20

The construction of the other two expression plasmids (FIG. 2, panels B and C) followed a similar strategy to that of c8αgluex1. The plasmid p5'αgluStuI was derived from p8,5αgluBSE by digestion of the plasmid with StuI, followed by self-ligation of the isolated fragment containing exon 2-3 plus the vector sequences. Plasmid p5'αgluStuI was digested with PglII followed by a partial digestion of the linear fragment with NcoI resulting in several fragments. The 2.4 kb fragment, containing exon 2 and 3, was isolated and ligated into the NcoI and BglII sites of vector pKUN12ΔC, resulting in p5'αgluex2. Note that pKUN12ΔC is a derivative of pKUN8ΔC containing the polylinker: ClaI NcoI BglII Hindi EcoRI SphI XhoI SmaI/SfiI NotI.

The plasmid p10αgluΔNotI was digested with BglII and HindIII. The fragment containing exons 16-20 was isolated and ligated in p5'αgluex2 digested with BglII and HindIII. The resulting plasmid was p5'3'αgluex2. The middle fragment in p5'3'αgluex2 was inserted as for pαgluex1. For this, p7.3αglu was digested with BglII. The fragment was isolated and ligated to the BglII-digested and dephosphorylated p5'3'αgluex2. The resulting plasmid, pαgluex2, was used in construction of c8αgluex-20 and c8,8αgluex2-20 (FIG. 2, panels B and C).

For the construction of third expression plasmid c8,8α gluex2-20 (FIG. 2, panel C) the 3' flanking region of α-glucosidase was deleted. To achieve this, pαgluex2 was digested with SphI. The fragment containing exon 2-20 was isolated and self-ligated resulting in pαgluex2-20. Subsequently, the fragment containing the 3' flanking region of bovine αS1-casein gene was isolated from p16,8αglu by digestion with SphI and NotI. This fragment was inserted into pαgluex2-20 using the SpII site and the NotI site in the polylinker sequence resulting in pαgluex2-20-3αS1.

The final step in generating c8,8αgluex2-20 was the ligation of three fragments as in the final step in the construction leading to c8αgluex1. Since the ClaI site in pαgluex2-20-3'αS1 and pαgluex2 appeared to be uncleavable due to methylation, the plasmids had to be propagated in the E. coli DAM(−) strain ECO343. The pαgluex2-20-3'αS1 isolated from that strain was digested with ClaI and NotI. The fragment containing exons 220 plus the 3' αS1-casein flanking region was purified from the vector sequences. This fragment, an 8 kb NotI-ClaI fragment containing the bovine αS1 promoter (see DeBoer (1991) and (1993), supra) and NotI-digested, dephosphorylated pWE15 were ligated and packaged. The resulting cosmid is c8,8αgluex2-20.

Cosmid c8αgluex2 (FIG. 2, panel B) was constructed via a couple of different steps. First, cosmid c8,8αgluex2-20 was digested with SalI and NotI. The 10.5-kb fragment containing the αS1-promoter and the exons 2-6 part of the acid α-glucosidase gene was isolated. Second, plasmid pαgluex2 was digested with SalI and NotI to obtain the fragment containing the 3' part of the acid α-glucosidase gene. Finally, the cosmid vector pWE15 was digested with NotI and dephosphorylated. These three fragments were ligated and packaged. The resulting cosmid is c8αgluex2.

Example 2

Transgenesis

The cDNA and genomic constructs were linearized with NotI and injected in the pronucleus of fertilized mouse oocytes which were then implanted in the uterus of pseudopregnant mouse foster mothers. The offspring were analyzed for the insertion of the human α-glucosidase cDNA or genomic DNA gene construct by Southern blotting of DNA isolated from clipped tails. Transgenic mice were selected and bred.

The genomic constructs linearized with NotI were also injected into the pronucleus of fertilized rabbit oocytes, which were implanted in the uterus of pseudopregnant rabbit foster mothers. The offspring were analyzed for the insertion of the alpha-glucosidase DNA by Southern blotting. Transgenic rabbits were selected and bred.

Example 3

Analysis of Acid α-glucosidase in the Milk of Transgenic Mice

Figure 4A:
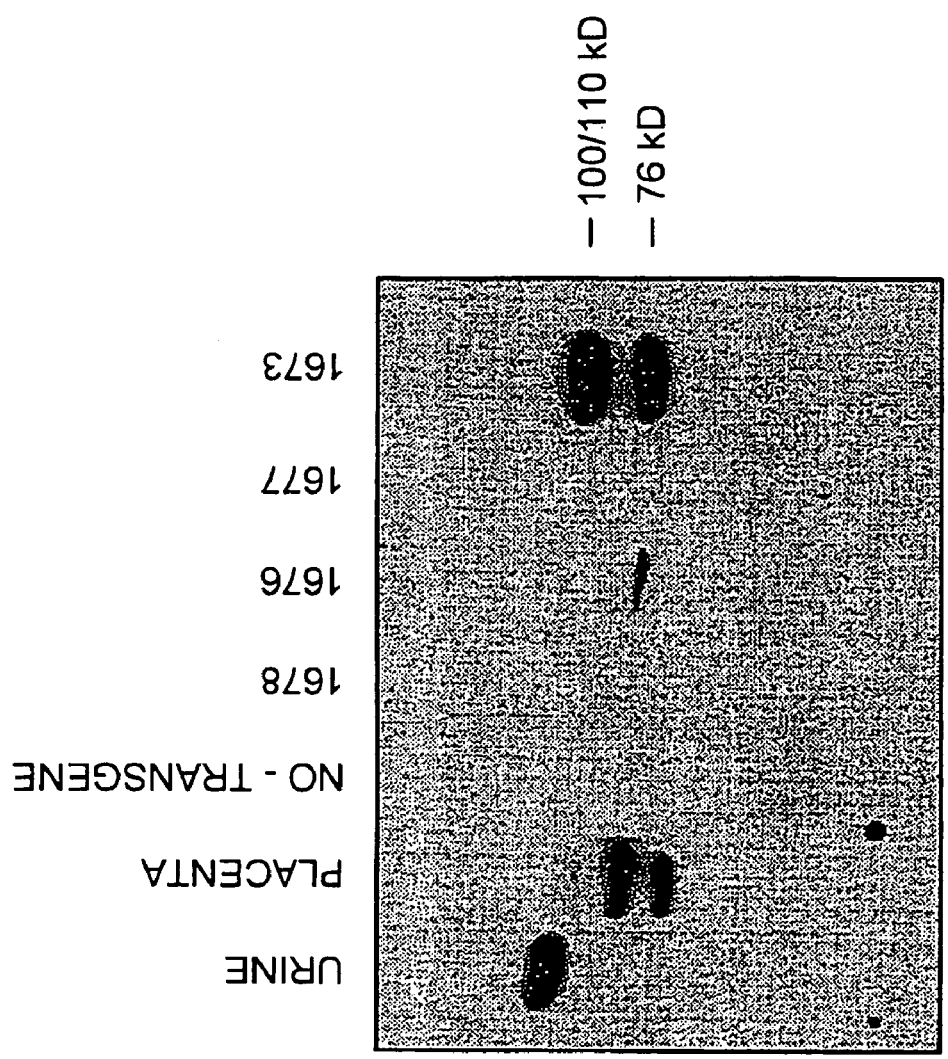
FIGS. 4A and 4B. Detection of acid α-glucosidase in milk of transgenic mice by Western blotting.
Figure 4B:
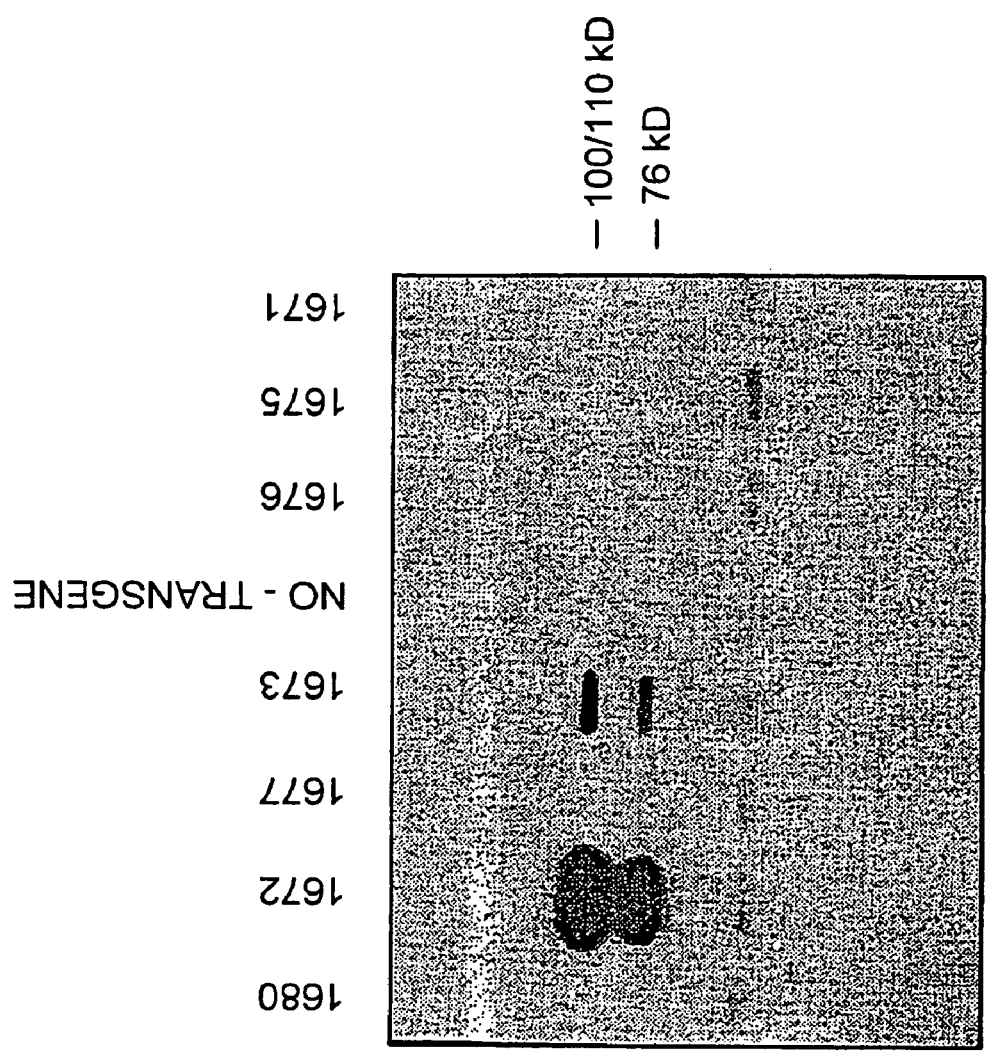

Milk from transgenic mice and nontransgenic controls was analyzed by Western Blotting. The probe was mouse antibody specific for human acid α-glucosidase (i.e., does not bind to the mouse enzyme). Transgenes 1672 and 1673 showed expression of human acid α-glucosidase in milk (FIGS. 4A and 4B). Major and minor bands at 100-110 kD and 76 kD were observed as expected for α-glucosidase. In milk from non-transgenic mice, no bands were observed.

The activity of human acid α-glucosidase was measured with the artificial substrate 4-methylumbelliferyl-α-D-glucopyranoside in the milk of transgenic mouse lines (See Galiaard, Genetic Metabolic Disease, Early Diagnosis and Prenatal Analysis, Elsevier/North Holland, Amsterdam, pp. 809-827 (1980)). Mice containing the cDNA construct (FIG. 1) varied from 0.2 to 2 .µmol/ml per hr. The mouse lines containing the genomic construct (FIG. 2, panel A) expressed at levels from 10 to 610 .µmol/ml per hr. These figures are equivalent to a production of 1.3 to 11.3 mg/l (cDNA construct) and 0.05 to 3.3 g/l (genomic construct) based on an estimated specific activity of the recombinant enzyme of 180 .µmol/mg (Van der Ploeg et al., J. Neurol. 235:392-396 (1988)).

The recombinant acid α-glucosidase was isolated from the milk of transgenic mice, by sequential chromatography of milk on ConA-Sepharose™ and Sephadex™ G200. 7 ml milk was diluted to 10 ml with 3 ml Con A buffer consisting of 10 mM sodium phosphate, pH 6.6 and 100 mM NaCl. A 1:1 suspension of Con A sepharose in Con A buffer was then added and the milk was left overnight at 4.degree. C. with gentle shaking. The Con A sepharose beads were then collected by centrifugation and washed 5 times with Con A buffer, 3 times with Con A buffer containing 1 M NaCl instead of 100 mM, once with Con A buffer containing 0.5 M NaCl instead of 100 mM and then eluted batchwise with Con A buffer containing 0.5 M NaCl and 0.1 M methyl-α-D-mannopyranoside. The acid α-glucosidase activity in the eluted samples was measured using the artificial 4-methyl-umbelliferyl-α-D-glycopyranoside substrate (see above). Fractions containing acid α-glucosidase activity were pooled, concentrated and dialyzed against Sephadex buffer consisting of 20 mM Na acetate, pH 4.5 and 25 mM NaCl, and applied to a Sephadex™ 200 column. This column was run with the same buffer, and fractions were assayed for acid α-glucosidase activity and protein content. Fractions rich in acid α-glucosidase activity and practically free of other proteins were pooled and concentrated. The method as described is essentially the same as the one published by Reuser et al., Exp. Cell Res. 155:178-179 (1984). Several modifications of the method are possible regarding the exact composition and pH of the buffer systems and the choice of purification steps in number and in column material.

Acid α-glucosidase purified from the milk was then tested for phosphorylation by administrating the enzyme to cultured fibroblasts from patients with GSD II (deficient in endogenous acid α-glucosidase). In this test mannose 6-phosphate containing proteins are bound by mannose 6-phosphate receptors on the cell surface of fibroblasts and are subsequently internalized. The binding is inhibited by free mannose 6-phosphate (Reuser et al., Exp. Cell Res. 155:178-189 (1984)). In a typical test for the phosphorylation of acid α-glucosidase isolated from milk of transgenic mice, the acid α-glucosidase was added to 104-106 fibroblasts in 500 .µl culture medium (Ham F10, supplied with 10% fetal calf serum and 3 mM Pipes) in an amount sufficient to metabolize 1 µmole 4-methyl-umbelliferyl-α-D-glucopyranoside per hour for a time period of 20 hours. The experiment was performed with or without 5 mM mannose 6-phosphate as a competitor, essentially as described by Reuser et al., supra (1984). Under these conditions acid α-glucosidase of the patient fibroblasts was restored to the level measured in fibroblasts from healthy individuals. The restoration of the endogenous acid α-glucosidase activity by acid α-glucosidase isolated from mouse milk was as efficient as restoration by acid α-glucosidase purified from bovine testis, human urine and medium of transfected CHO cells. Restoration by α-glucosidase form milk was inhibited by 5 mM mannose 6-phosphate as observed for α-glucosidase from other sources. (Reuser et al., supra; Van der Ploeg et al., (1999), supra; Van der Ploeg et al., Ped. Res. 24:90-94 (198B).

As a further demonstration of the authenticity of α-glucosidase produced in the milk, the N-terminal amino acid sequence of the recombinant α-glucosidase produced in the milk of mice was shown to be the same as that of α-glucosidase precursor from human urine as published by Hoefsloot et al., EMBO J. 7:1697-1704 (1988) which starts with AHPGRP (SEQ ID NO:1).

Example 4

Animal Trial of Alpha-Glucosidase

Recently, a knock-out mouse model for Pompe's disease has become available (25) This model was generated by targeted disruption of the murine alpha-glucosidase gene. Glycogen-containing lysosomes are detected soon after birth in liver, heart and skeletal muscle. Overt clinical symptoms only become apparent at relatively late age (>9 months), but the heart is typically enlarged and the electrocardiogram is abnormal.

Experiments have been carried out using the knock-out (KO) mouse model in order to study the in vivo effect of AGLU purified from transgenic rabbit milk. The recombinant enzyme in these experiments was purified from milk of the transgenic rabbits essentially as described above for purification from transgenic mice.

1. Short Term Studies in KO Mouse Model

Single or multiple injections with a 6 day interval were administered to KO mice via the tail vein. Two days after the last enzyme administration the animals were killed, and the organs were perfused with phosphate buffered saline (PBS). Tissue homogenates were made for GLU enzyme activity assays and tissue glycogen content, and ultrathin sections of various organs were made to visualize accumulation (via electron microscopy) lysosomal glycogen content. Also the localization of internalized AGLU was determined using rabbit polyclonal antibodies against human placenta mature α-glucosidase.

The results showed that single doses of 0.7 and 1.7 mg AGLU (experiments C and A respectively) was taken up efficiently in vivo in various organs of groups of two knock-out mice when injected intravenously. Experiment A also showed that there were no differences in the uptake and distribution of AGLU purified from two independent rabbit milk sources.

Increases in AGLU activity were seen in the organs such as the liver, spleen, heart, and skeletal muscle, but not in the brain. Two days after a single injection of 1.7 mg AGLU to two KO animals, levels close to, or much higher than, the endogenous alpha-glucosidase activity levels observed in organs of two PBS-injected normal control mice or two heterozygous KO mice were obtained (experiment A). Of the organs tested, the liver and spleen are, quantitatively, the main organs involved in uptake, but also the heart and pectoral and femoral muscles take up significant amounts of enzyme. The absence of a significant increase in brain tissue suggests that AGLU does not pass the blood-brain barrier. The results are summarized in Table 2.

Immunohistochemical staining of AGLU was evident in lysosomes of hepatocytes using a polyclonal rabbit antibody against human alpha-glucosidase. The presence of AGLU in heart and skeletal tissues is more difficult to visualize with this technique, apparently due to the lower uptake.

2. Long-Term Experiments with the KO Mouse Model

In longer term experiments, enzyme was injected in the tail vein of groups of two or three KO mice, once a week for

TABLE 2

Tissue Uptake of AGLU and Glycogen Content Following Short Term Treatment in KO Mouse Model

| Group | Liver | | Spleen | | Heart | | Pectoral Muscle | | Femoral Muscle | | Tongue | | Brain | |
|---|---|---|---|---|---|---|---|---|---|---|---|---|---|---|
| | Act | Glc | Act | Glc | Act | Glc | Act | Glc | Act | Glc | Act | Glc | Act | Glc |
| Experiment A animals treated with single dose of 1.7 mg AGLU (from 2 sources) | | | | | | | | | | | | | | |
| treated KO mice source 1 | 674 | — | — | — | 263 | — | — | — | 24 | — | — | — | 0.8 | — |
| | 410 | | | | 17 | | | | 3.1 | | | | 0.4 | |
| treated KO mice source 2 | 454 | — | — | — | 76 | — | — | — | 12 | — | — | — | 0.8 | — |
| | 604 | | | | 48 | | | | 10 | | | | 0.4 | |
| untreated KO mouse | 3.1 | — | — | — | 0.2 | — | — | — | 0.2 | — | — | — | 0.2 | — |
| untreated normal mouse | 58 | — | — | — | 23 | — | — | — | 11 | — | — | — | 57 | — |
| | 37 | | | | 17 | | | | 8.2 | | | | 57 | |
| Experiment B animals treated with 4 doses of AGLU (1.0, 2.0, 1.0 and 1.4 mg.) 6 days apart | | | | | | | | | | | | | | |
| treated KO mice (13 weeks old) | 1132 | 70 | — | — | 24 | 1259 | 125 | 87 | — | — | 89 | — | 0.4 | 163 |
| | 944 | 13 | | | 10 | 1082 | 46 | 116 | | | 35 | | 0.2 | 163 |
| treated KO mice (34 weeks old) | 3375 | 23 | — | — | 60 | 1971 | 49 | 90 | — | — | 207 | — | 0.7 | 374 |
| untreated KO mice (13 and 34 weeks old) | 2.0 | 406 | — | — | 0.2 | 3233 | 1.0 | 86 | — | — | 1.0 | — | 0.2 | 487 |
| | 2.0 | 147 | | | 0.3 | 1748 | 1.0 | 87 | | | 1.0 | | 0.2 | 168 |
| untreated normal mice (34 weeks old) | 35 | 6 | — | — | 8.2 | 0 | 6.0 | 1.0 | — | — | 14 | — | 18 | 0 |
| treated KO mice | 582 | — | 462 | — | 46 | — | — | — | 5.1 | — | — | — | 0.4 | — |
| | 558 | | 313 | | 50 | | | | 3.6 | | | | 0.4 | |
| untreated KO mice | 1.1 | — | 0.8 | — | 0.3 | — | — | — | 0.2 | — | — | — | 0.2 | — |
| | 1.6 | | 0.7 | | 0.3 | | | | 0.3 | | | | 0.2 | |

Figures in the table refer to individual animals
Act: AGLU activity (nmoles 4MU per mg protein per hour)
GLC: Glycogen content (μg/mg protein)
n.d. not detected
— data unavailable When two KO mice were injected 4 times every 6 days (experiment B), a marked decrease of total cellular glycogen was observed in both heart and liver. No effects were observed in skeletal muscle tissues with regard to total glycogen. However, in general the uptake of AGLU in these tissues was lower than in the other tissues tested.

Transmission electron microscopy of the 4 times injected KO mice indicated a marked decrease in lysosomal glycogen in both liver cells and heart muscle cells. The effects observed in heart tissue are localized since in some areas of the heart no decrease in lysosomal glycogen was observed after these short term administrations.

Western blot analysis using rabbit polyclonal antibodies against human placenta mature alpha-glucosidase indicated complete processing of the injected AGLU towards the mature enzyme in all organs tested strongly suggesting uptake in target tissues, and lysosomal localization and processing. No toxic effects were observed in any of the three experiments.

periods of up to 25 weeks. The initial dose was 2 mg (68 mg/kg) followed by 0.5 mg (17 mg/kg)/mouse for 12 weeks. In two groups of mice, this was followed by either 4 or 11 additional weeks of treatment of 2 mg/mouse. Injections started when the mice were 6-7 months of age. At this age, clear histopathology has developed in the KO model. Two days after the last enzyme administration the animals were killed, and the organs were perfused with phosphate buffered saline (PBS). Tissue homogenates were made for AGLU enzyme activity assays and tissue glycogen content, and sections of various organs were made to visualize (via light microscopy) lysosomal glycogen accumulation.

The results showed that mice treated 13 weeks with 0.5 mg/mouse (Group A, 3 animals/Group) had an increase of activity in the liver and spleen and decreased levels of glycogen in liver and perhaps in heart. One animal showed increased activity in muscles, although there was no significant decrease of glycogen in muscle.

Mice that were treated 14 weeks with 0.5 mg/mouse followed by 4 weeks with 2 mg/mouse (Group B, 3 animals/

Group) showed similar results to those treated for 13 weeks only, except that an increased activity was measured in the heart and skeletal muscles and decreases of glycogen levels were also seen in the spleen.

Mice that were treated 14 weeks with 0.5 mg/mouse followed by 11 weeks with 2 mg/mouse (Group C 2 animals/Group) showed similar results to the other two groups except that treated mice showed definite decreases in glycogen levels in liver, spleen, heart and skeletal muscle. No activity could be detected, even at the highest dose, in the brain.

Results of treated and untreated animals in each Group (Group means) are summarized in Table 3.

C
100 mg: Group 2, treatment period 1
D
200 mg: Group 3, treatment period b 1
E
400 mg: Group 2, treatment period 2
F
800 mg: Group 3, treatment period 2
P
placebo (1 subject per Group and treatment period)

Subjects were administered AGLU or placebo as an infusion on Day 1 of each treatment period. The infusions were

TABLE 3

Tissue Uptake of AGLU and Glycogen Content Following Long Term Treatment in KO Mouse Model

| Group | Liver Act | Liver Glc | Spleen Act | Spleen Glc | Heart Act | Heart Glc | Pectoral Muscle Act | Pectoral Muscle Glc | Quadriceps Muscle Act | Quadriceps Muscle Glc | Gastroenemius Muscle Act | Gastroenemius Muscle Glc | Brain Act | Brain Glc |
|---|---|---|---|---|---|---|---|---|---|---|---|---|---|---|
| Group A animals treated with 0.5 mg/mouse/week for 13 weeks |
| treated | 713 | 2 | 463 | n.d. | 3 | 86 | 9 | 81 | 6 | 40 | 14 | 66 | — | — |
| untreated | 2 | 24 | 1 | n.d. | 1 | 111 | 1 | 66 | 1 | | 1 | 61 | — | — |
| Group B animals treated with 0.5 mg/mouse/week for 14 weeks, followed by 2 mg/mouse/week for 4 weeks |
| treated | 2705 | 1 | 1628 | 0 | 59 | 288 | 49 | 120 | 30 | 128 | 44 | 132 | — | — |
| untreated | 3 | 11 | 31 | 6 | 1 | 472 | 1 | 113 | 1 | 162 | 1 | 142 | — | — |
| Group C animals treated with 0.5 mg/mouse/week for 14 weeks, followed by 2 mg/mouse/week for 11 weeks |
| treated | 1762 | 1 | 1073 | 2 | 66 | 211 | 99 | 113 | 37 | 18 | 109 | 32 | 1 | 32 |
| untreated | 2 | 45 | 1 | 21 | 1 | 729 | 1 | 291 | 0 | 104 | 0 | 224 | 0 | 44 |

Figures in the table refer to the mean of 3 animals (Groups A and B) or the mean of 2 animals (Group C)
Act: AGLU activity (nmoles 4MU per mg protein per hour)
GLC: Glycogen content (μg/mg protein)
n.d. not detected
— data unavailable In addition, a very convincing improvement in the histopathological condition was observed in Group C mice (treated for the first 14 weeks at 0.5 mg/mouse, followed by 11 weeks at 2 mg/mouse). Clear reversal of pathology was demonstrated in various tissues, such as heart and pectoralis muscle.

It has been reported that Pompe's disease does not occur when the residual lysosomal α-glucosidase activity is >20% of average control value (14). The data obtained with the KO mouse model indicates that these levels are very well achievable using recombinant precursor enzyme.

Example 5

Human Clinical Trial

A single phase I study (AGLUI 101-01) has been conducted in 15 healthy male volunteers. Doses of AGLU ranged from 25 to 800 mg, administered by intravenous infusion to healthy male adult volunteers. Subjects with a history of allergies and hypersensitivities were excluded from the study. The subjects were randomized into dose groups of 5, and each dose Group received AGLU (4 subjects) or placebo (1 subject) at each dose level. All subjects received two doses of study drug, which were administered two weeks apart. The dosing regimen was as follows:
A
25 mg: Group 1, treatment period 1
B
50 mg: Group 1, treatment period 2 administered over a 30 minute period and subjects were kept in a semi-recumbent position for at least 2 hours after cessation of infusion.

Adverse events were recorded just before the start of the infusion, at 30 minutes (end of infusion) and at 3, 12, 24, 36 and 48 hours thereafter as well as on Days 5 and 8 (first period) and days 5, 8 and 15 (second period). Vital signs, ECG and physical examinations were also monitored regularly throughout the treatment period.

Blood samples were taken for a standard range of clinical laboratory tests and pharmacokinetics analysis. The subject's urine was collected and a standard range of laboratory analyses (including determination of AGLU) were performed.

(a) Laboratory Safety and Adverse Events

There were no clinically significant changes in laboratory parameters, clinical signs and ECG measurements in any subjects at any dose Group. The results of adverse event monitoring in all subjects at all doses are summarized in Table 4.

TABLE 4

Adverse Event Reports

| Dose (mg) | Adverse Events |
|---|---|
| 25 | The reported events were muscle weakness, abnormal vision and fatigue. All events were mild and were deemed unrelated to the test article by the investigator |

TABLE 4-continued

Adverse Event Reports

| Dose (mg) | Adverse Events |
|---|---|
| 50 | The reported events were headache, rhinitis, nose bleed and paresthesia. All events were mild and were deemed unrelated or remotely related to the test article by the investigator, except the paresthesia which was classed as moderate and was deemed possibly related to the test article. |
| 100 | The reported events were rhinitis, headache, fatigue, hematoma and injection site reaction. All events were classed as mild. The cases of hematoma, injection site reaction and intermittent headache were deemed possibly or probably related to the test article by the investigator. The other events were deemed to be unrelated. |
| 200 | The reported events were nausea, headache, dizziness, fatigue, rhinitis, photophobia, vision abnormalities and euphoria. All events were classed as mild or moderate in intensity. Seven events (including cases of dizziness, nausea and abnormal vision) were deemed to be possibly or probably related to the test article. |
| 400 | The reported events were fatigue and paresthesia. The report of fatigue was considered unrelated to the test article, and the paresthesia was deemed possibly related. |
| 800 | The reported events were nausea, drowsiness, dizziness, increased sweating, asthenia, shivering and intermittent headache. All events were classed as mild or moderate in intensity. Eight events (including cases of drowsiness, nausea and asthenia) were deemed to be possibly related to the test article. |

A trial of the safety and efficacy of recombinant acid α-glucosidase as enzyme replacement therapy on infantile and juvenile patients with glycogen storage disease Type II is conducted. Four infantile patients and three juvenile patients are recruited. Infantiles are administered a starting dose of 15-20 mg/kg titrated to 40 mg/kg and juveniles are administered 10 mg/kg. Patients are treated for 24 weeks.
Patients are evaluated by the following parameters.
Standard adverse event reporting including suspected adverse events
Laboratory parameters including hematology, clinical chemistry and antibody detection.
α-glucosidase activity in muscle
Muscle histopathology
12-lead ECG
Clinical condition including neurological examination
Non-parametric PK parameters
Life saving interventions Infantile patients are evaluated for the following additional parameters.
Left posterior ventricular wall thickness and left ventricular mass index
Neuromotor development
Survival
Glycogen content in muscle Juvenile patients are evaluated for the following additional parameters.
Pulmonary function
Muscle strength/timed tests and muscle function
PEDI/Rotterdam 9-item scale The same patients are then subject to additional dosages of alpha glucosidase with infantiles receiving 15, 20, 30 or 40 mg/kg and juveniles: 10 mg/kg for an additional period of 24 weeks and evaluated by the parameters indicated above.

A further phase II clinical trial is performed on eight patients aged <6 months of age within 2 months after diagnosis at a dosage of 40 mg/kg. Patients are treated for 24 weeks and evaluated by the following criteria:
Safety parameters
Laboratory safety data
Adverse event recording
Primary efficacy parameter: survival without life-saving interventions (i.e. mechanical ventilation >24 hr) 6 months past diagnosis in combination with normal or mildly delayed motor function (BSID II).
Secondary efficacy: Changes in neuromotor development, changes in left posterior ventricular wall thickness and left ventricular mass index; Changes in skeletal muscle acid α-glucosidase activity and glycogen content.
Efficacy can be show by a 50% survival at 6 months post-diagnosis without life saving interventions in the α-glucosidase group compared to 10% survival in the historical control group in combination with a BSID II classified as normal or mildly delayed.

A further clinical trial is performed on juvenile patients. The patients are aged >1 year and <35 years of age with juvenile onset of GSD type IIb The patients are administered 10 mg/kg or 20 mg/kg for a period of twenty-four weeks treatment. Treatment is monitored by the following parameters.

| Safety parameters | Laboratory safety data Adverse event recording |
|---|---|
| Primary efficacy | Pulmonary function parameters (e.g. FVC, time on ventilator) Muscle strength |
| Secondary efficacy | Life-saving interventions parameters: Quality of life Skeletal muscle acid α-glucosidase activity |
| Quantitative objective | 20% relative improvement in primary efficacy parameters over baseline |

All quantitative measurements relating to efficacy are preferably statistically significant relative to contemporaneous or historical controls, preferably at p<0.05.

Example 6

Pharmaceutical Formulations

Alpha-glucosidase is formulated as follows: 5 mg/ml α-Glu, 15 mM sodium phosphate, pH 6.5, 2% (w/w) mannitol, and 0.5% (w/w) sucrose. The above formulation is filled to a final volume of 10.5 ml into a 20 cc tubing vial and lyophilized. For testing, release and clinical use, each vial is reconstituted with 10.3 ml* of sterile saline (0.9%) for injection (USP or equivalent.) to yield 10.5 ml of a 5 mg/ml α-Glu solution that may be directly administered or subsequently diluted with sterile saline to a patient specific target dose concentration. The 10.5 ml fill (52.5 mg alpha glucosidase total in vial) includes the USP recommended overage, that allows extraction and delivery (or transfer) of 10 mls (50 mg). The mannitol serves as a suitable bulking agent shortening the lyophilization cycle (relative to sucrose alone). The sucrose serves as a cryo/lyoprotectant resulting in no significant increase in aggregation following reconstitution. Reconstitution of the mannitol (only) formulations had repeatedly resulted in a slight increase in aggregation. Following lyophilization, the cake quality was acceptable and subsequent reconstitution times were significantly reduced Saline is preferred to HSA/dextrose for infusion solution. When saline is used in combination with lyophilization in 2% mannitol/ 0.5% sucrose the solution has acceptable tonicity for intravenous administration. The lyophilized vials containing the 2% mannitol/0.5% sucrose formulation were reconstituted with 0.9% sterile saline (for injection) to yield 5 mg/ml α-Glu.

Example 7

Infusion Schedule

The solution is administered via the indwelling intravenous cannula. Patients are monitored closely during the infusion period and appropriate clinical intervention are taken in the event of an adverse event or suspected adverse event. A window of 48 hours is allowed for each infusion. An infusion schedule in which the rate of infusion increases with time reduces or eliminates adverse events.

Infusions for infantiles can be administered according to the following schedule:

5 cc/hr for 60 minutes 10 cc/hr for 60 minutes gtoreq.40 cc/hr for 30 minutes gtoreq.80 cc/hr for the remainder of the infusion Infusions for juveniles can be administered according to the following schedule:

0.5 cc/kg/hr for 60 minutes 1 cc/kg/hr for 60 minutes 5 cc/kg/hr for 30 minutes 7.5 cc/kg hr for the remainder of the infusion While the foregoing invention has been described in some detail for purposes of clarity and understanding, it will be clear to one skilled in the art from a reading of this disclosure that various changes in form and detail can be made without departing from the true scope of the invention. All publications and patent documents cited in this application are incorporated by reference in their entirety for all purposes to the same extent as if each individual publication or patent document were so individually denoted.

---

---

What is claimed is:

1. A method of treating a human patient with Pompe's disease, comprising administering intravenously to the patient a therapeutically effective amount of human acid alpha glucosidase, whereby the concentration of accumulated glycogen in the patient is reduced and/or further accumulation of glycogen is arrested.

2. The method of claim 1, wherein the alpha-glucosidase is produced in milk of a transgenic mammal.

3. The method of claim 1, wherein the alpha-glucosidase is predominantly in a 110 kD form.

4. The method of claim 1, wherein the alpha-glucosidase is administered weekly.

5. The method of claim 4, wherein the therapeutically effective amount of human acid alpha-glucosidase is at least 10 mg/kg body weight of the patient.

6. A method of treating a human patient with Pompe's disease, comprising intravenously administering biweekly to the patient a therapeutically effective amount of human acid alpha glucosidase, whereby hypertrophic cardiomyopathy in the patient is reduced and/or arrested.

* * * * *

SEQUENCE LISTING

```
<160> NUMBER OF SEQ ID NOS: 3

<210> SEQ ID NO 1
<211> LENGTH: 6
<212> TYPE: PRT
<213> ORGANISM: Artificial Sequence
<220> FEATURE:
<223> OTHER INFORMATION: N-terminal of recombinant alpha-glucosidase

<400> SEQUENCE: 1

Ala His Pro Gly Arg Pro
 1               5

<210> SEQ ID NO 2
<211> LENGTH: 36
<212> TYPE: DNA
<213> ORGANISM: Artificial Sequence
<220> FEATURE:
<223> OTHER INFORMATION: Figure 1: flanking sequence

<400> SEQUENCE: 2
ctcgagtatc gattgaattc atctgtcgac gctacc                              36

<210> SEQ ID NO 3
<211> LENGTH: 18
<212> TYPE: DNA
<213> ORGANISM: Artificial Sequence
<220> FEATURE:
<223> OTHER INFORMATION: Figure 1: flanking sequence

<400> SEQUENCE: 3
gcatgcctcg acggtacc                                                  18
```